(12) United States Patent
Kingston et al.

(10) Patent No.: US 7,560,536 B2
(45) Date of Patent: Jul. 14, 2009

(54) MORNING GLORY-DERIVED ANTICANCER AGENTS, AND NOVEL IPOMOEASSIN COMPOUNDS

(75) Inventors: David G. I. Kingston, Blacksburg, VA (US); Shugeng Cao, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 165 days.

(21) Appl. No.: 11/366,806

(22) Filed: Mar. 3, 2006

(65) Prior Publication Data

US 2006/0264383 A1   Nov. 23, 2006

Related U.S. Application Data

(60) Provisional application No. 60/681,944, filed on May 18, 2005.

(51) Int. Cl.
    *C07H 17/08* (2006.01)
(52) U.S. Cl. ........................................... 536/6.5
(58) Field of Classification Search ............... 536/6.5, 536/4.1, 1.11
    See application file for complete search history.

(56) References Cited

FOREIGN PATENT DOCUMENTS

WO   WO 2004/019961   *   3/2004

OTHER PUBLICATIONS

Cao, S, Guza, RC, Wisse, JH, Miller, JS, Evans, R, Kingston, DG (Apr. 2005) ipomoeassins A-E, Cytotoxic Macrocyclic Glycoresins from the Leaves of Ipomoea squamosa from the Suriname Rainforest, Journal of Natural Products, v. 68, issue 4, p. 487-492.*

Barnes, CC, Smailey, MK, Manfredi, KP, Kindscher, K, Loring, H, Sheeley, DM (2003) Characterization of an Anti-tuberculosis Resin Glycoside from the Prairie Medicinal Plant Ipomoea Ieptophylla, Journal of Natural Products, v. 66, p. 1457-1462.*

Umehara et al. "Isolation of a new 15-membered macrocyclic glycolipid lactone, cuscutic resinoside A from the seeds of cuscutic chinensis: A stimulator of breast cancer cell proliferation" pp. 299-304; 2004.

Abstracts, American Chemical Society; Division of Medicinal Chemistry.

Abstract Submission Form, International Congress on Natural Products Research Jul. 31-Aug. 4, 2004.

Leon et al. "Journal of Natural Products" vol. 68, No. 8; Aug. 2005.

* cited by examiner

*Primary Examiner*—Shaojia Anna Jiang
*Assistant Examiner*—Scarlett Goon
(74) *Attorney, Agent, or Firm*—Whitham Curtis Christofferson & Cook, P.C.

(57) ABSTRACT

Ipomoeassin compounds derived from morning glory plant material (especially *Ipomoea* sp. from Suriname) are useful as anti-cancer agents. The novel compounds also are useful for treating neurodegenerative disorders (such as Alzheimer's disease) in human patients.

3 Claims, 14 Drawing Sheets

MORNING GLORY-DERIVED ANTICANCER AGENTS, AND NOVEL IPOMOEASSIN COMPOUNDS

RELATED APPLICATION

This application claims benefit of U.S. provisional application No. 60/681,944 filed May 18, 2005 titled "Constituents of morning glory as anticancer agents."

STATEMENT REGARDING GOVERNMENT FUNDING

This work was supported by the International Cooperative Biodiversity Grant Number TW 00313 from the Fogarty Center, National Institutes of Health.

BACKGROUND

About 650 species of Morning Glories (*Ipomoea* sp., family Convolvulaceae) are distributed across the world's tropical and subtropical regions, and more than 300 species come from the Americas alone. *Ipomoea batatas* (L.) Lam. is the common sweet potato. Most species of *Ipomoea* are vines, a small group of Neotropical species are small trees, but most have characteristic funnel-shaped flowers that open in early morning and last a single day. The genus *Ipomoea* has afforded glycoresins which are usually composed of a few sugars and one or more long chain fatty acid(s). (Noda, N.; Ono, M.; Miyahara, K.; Kawasaki, T.; Okabe, M., *Tetrahedron* 1987, 43, 3889-3902; Noda, N.; Tsuji, K.,.; Miyahara, K.; Yang, C. R., *Chem. Pharm. Bull.* 1994, 42, 2011-2016; Pereda-Miranda, R.; Mata, R.; Anaya, A. L.; Wickramaratne, D. B. M.; Pezzuto, J. M.; Kinghorn, A. D., *J. Nat. Prod.* 1993, 56, 571-582; Bah, M.; Pereda-Miranda, R., *Tetrahedron* 1996, 52, 13063-13080; Bah, M.; Pereda-Miranda, R., *Tetrahedron* 1997, 53, 9007-9022; Hernandez-Carlos, B.; Bye, R.; Pereda-Miranda, R., *J. Nat. Prod.* 1999, 62, 1096-1100; Barnes, C. C.; Smalley, M. K.; Manfredi, K. P.; Kindscher, K.; Loring, H.; Sheeley, D. M., *J. Nat. Prod.,* 2003, 66, 1457-1462; Leon, I.; Enriquez, R. G., Gnecco, D., Villarreal, M. L., Cortes, D. A.; Reynolds, W. F.; Yu, M, *J. Nat. Prod.,* 2004, 67, 1552-1556.) The purgative properties of some *Ipomoea* sp. are due to the presence of glycolipids in their resins. Noda (1987), supra; Bah (1996), supra. It has been reported that *Ipomoea leptophylla* showed activity against *Mycobacterium tuberculosis*. (Barnes et al, supra.) *Ipomoea squamosa* Choisy is a vine that is widespread in the Neotropics. The constituents of Morning Glories have been recently reviewed. (Pereda-Miranda, R., Bah, M., *Curr. Top. Med. Chem.,* 2003, 3, 111-131.)

By way of background, other *Ipomoea* plant materials are being studied. See Leon, I.; Enriquez, R. G.; Nieto, D. A.; Alonso, D.; Reynolds, W. F.; Aranda, E. and Villa, J., Pentasaccharide glyosides from the roots of *Ipomoea murocoides, J. Nat. Prod.* 2005, 68, 1141-1146. See also Umehara, K.; Nemoto, K; Ohkubo, T.; Miyase, T.; Degawa, M.; Noguchi, H., *Planta Medica* 2004, 70, 299-304.

SUMMARY OF THE INVENTION

The present inventors have invented a series of ipomoeassin compounds. "Ipomoeassin," which is relatively new terminology to the literature, as used herein means a substituted disaccharide with a long chain substituted or unsubstituted hydroxyacid linking the two carbohydrate residues, obtained from a plant of the *Ipomoea* genus.

The invention in a first preferred embodiment provides the following novel compounds:

(1) a compound of structure 1:

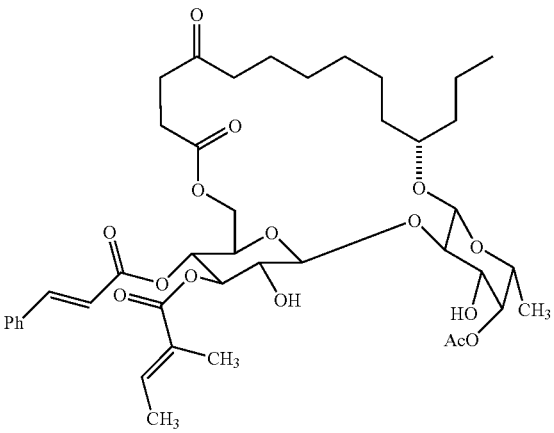

1

(2) a compound of structure 2:

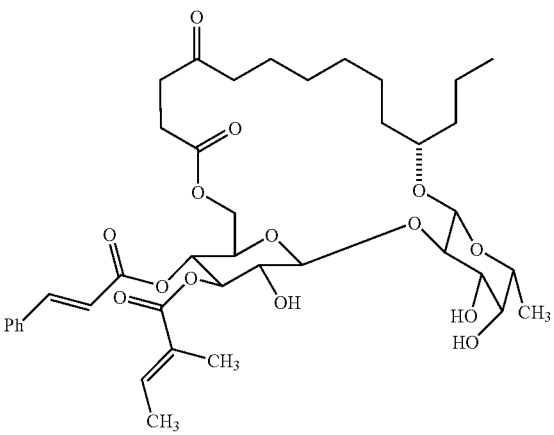

2

(3) a compound of structure 3:

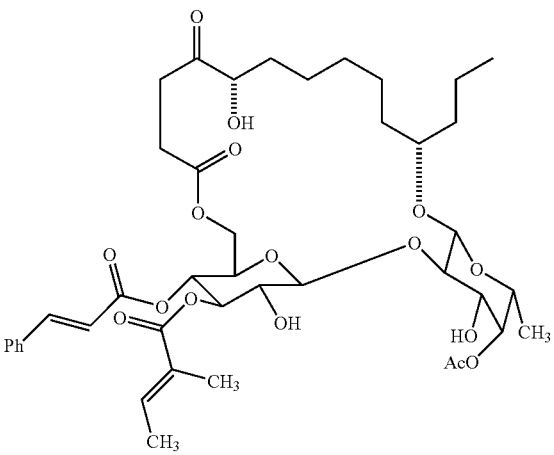

3

(4) a compound of structure 4:

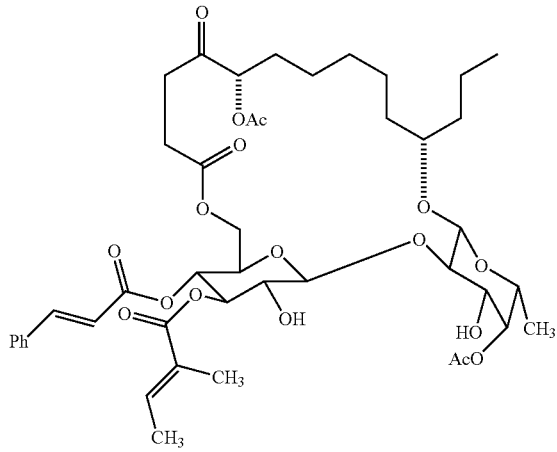

(5) a compound of structure 5:

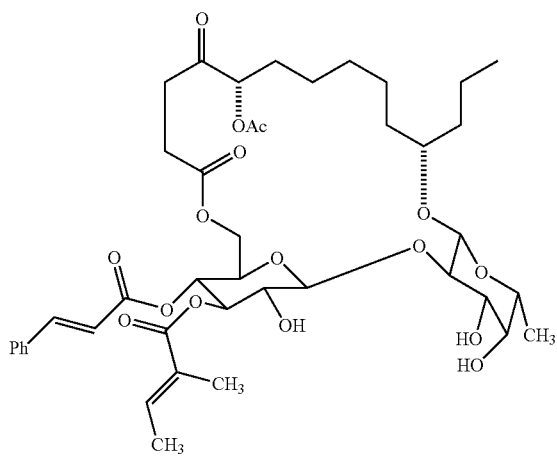

(6) a compound of structure 6:

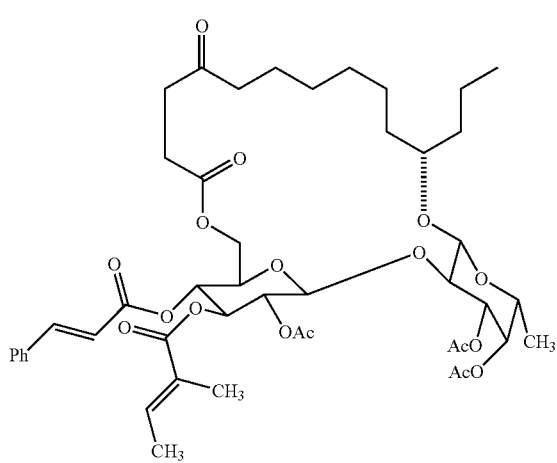

(7) a compound of structure 7:

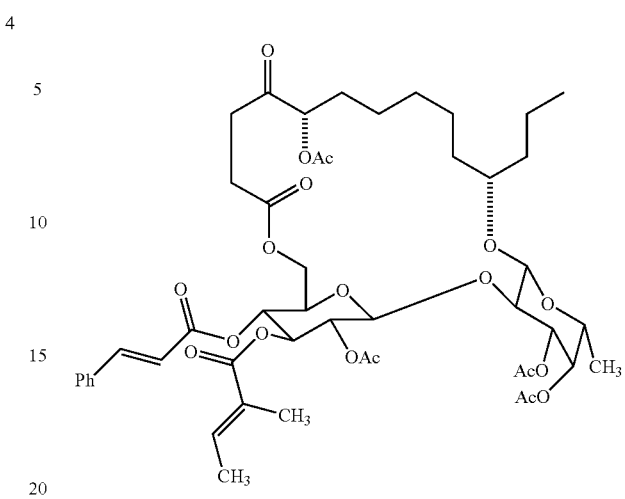

(8) a compound of structure 14:

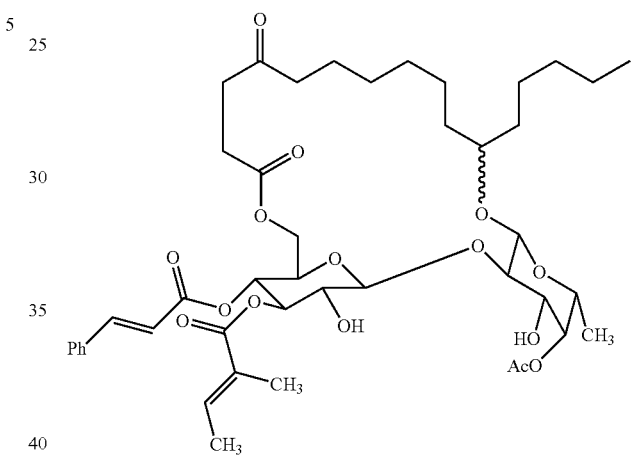

(9) A compound of structure 15:

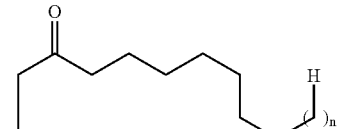

wherein $R^2$, $R^3$, and $R^4$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups. $R^2$, $R^3$, and $R^4$ can be the same or different groups, and n can be any integer from 0 to 10;

(10) a compound of structure 16:

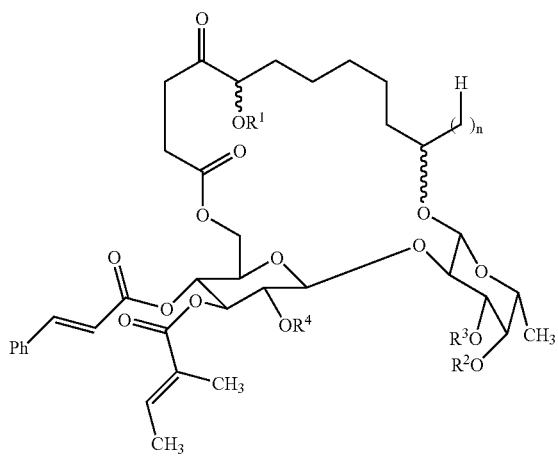

16 wherein $R^1$, $R^2$, $R^3$, and $R^4$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups. $R^1$, $R^2$, $R^3$, and $R^4$ can be the same or different groups, and n can be any integer from 0 to 10;

(11) a compound of structure 17:

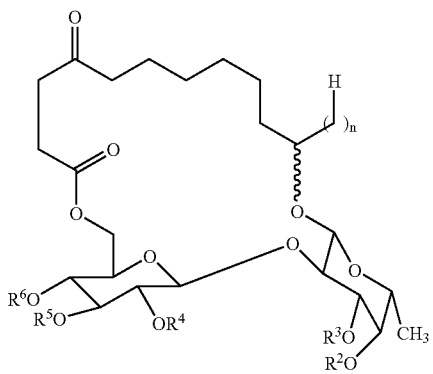

17 wherein $R^2$, $R^3$, $R^4$, $R^5$, and $R^6$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups. $R^2$, $R^3$, $R^4$, $R^5$, and $R^6$ can be the same or different groups, and n can be any integer from 0 to 10;

(12) a compound of structure 18:

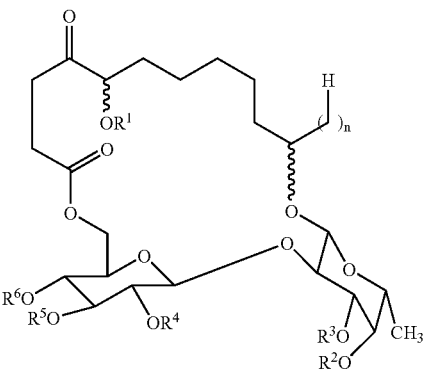

18 wherein $R^1$, $R^2$, $R^3$, $R^4$, $R^5$, and $R^6$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups. $R^1$, $R^2$, $R^3$, $R^4$, $R^5$, and $R^6$ can be the same or different groups, and n can be any integer from 0 to 10;

(13) a compound of structure 19:

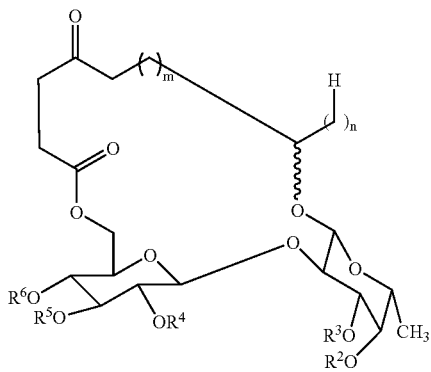

19 where $R^2$, $R^3$, $R^4$, $R^5$, and $R^6$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups. $R^2$, $R^3$, $R^4$, $R^5$, and $R^6$ can be the same or different groups, and m and n can be any integers from 0 to 10;

(14) a compound of structure 20:

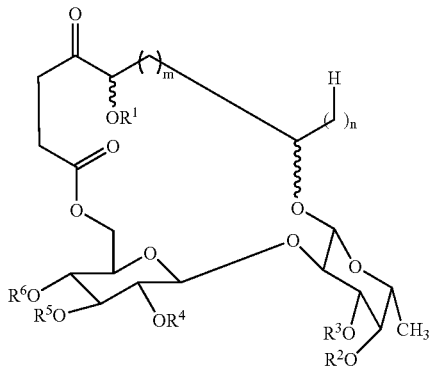

20 wherein $R^1$, $R^2$, $R^3$, $R^4$, $R^5$, and $R^6$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups. $R^1, R^2, R^3, R^4, R^5$, and $R^6$ can be the same or different groups, and m and n can be any integers from 0 to 10;

(15) a compound of structure 21:

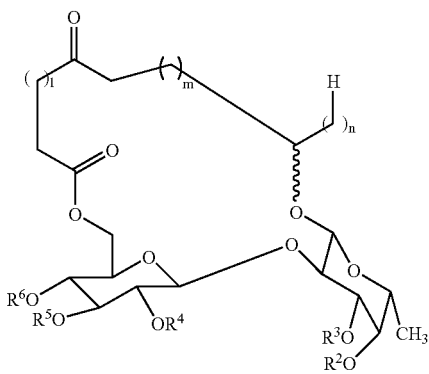

21 wherein $R^2, R^3, R^4, R^5$, and $R^6$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, or a combination of alkyl and aryl groups; $R^2, R^3, R^4, R^5$, and $R^6$ can be the same or different groups, and l, m and n can be any integers from 0 to 10;

(16) a compound of structure 22:

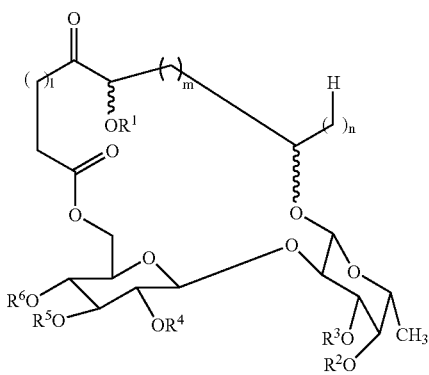

22 wherein $R^1, R^2, R^3, R^4, R^5$, and $R^6$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups; $R^1, R^2, R^3, R^4, R^5$, and $R^6$ can be the same or different groups, and l, m and n can be any integers from 0 to 10;

(17) a compound of structure 23:

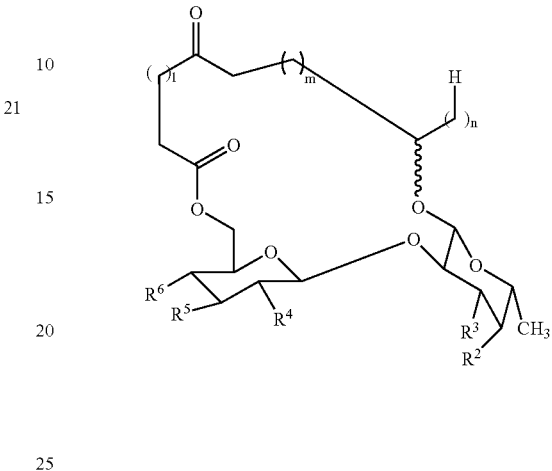

23 wherein $R^2, R^3, R^4, R^5$, and $R^6$ can variously be hydrogen or can be drawn from the groups R, where R can be any $C_1$ to $C_{12}$ straight chain or branched alkyl group, any nitrogen-containing group, any aryl group, any alkoxy, any alkylthio, any haloalkoxy, any haloalkylthio, or any alkenyl group in which the double bond can be variously substituted with $C_1$ to $C_6$ alkyl groups, aryl groups, or a combination of alkyl and aryl groups; $R^2, R^3, R^4, R^5$, and $R^6$ can be the same or different groups, and l, m and n can be any integers from 0 to 10;

(18) a compound of structure 24:

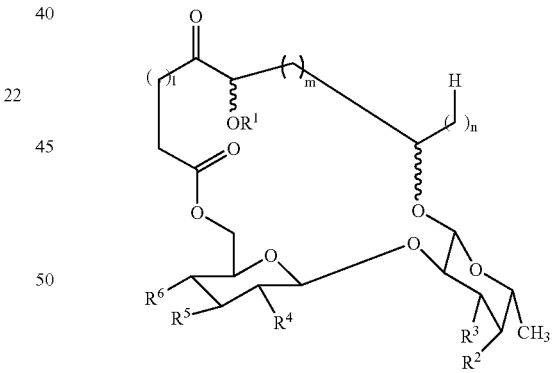

24 wherein $R^1, R^2, R^3, R^4, R^5$, and $R^6$ can variously be hydrogen or can be drawn from the groups R, where R can be any $C_1$ to $C_{12}$ straight chain or branched alkyl group, any nitrogen-containing group, any aryl group, any alkoxy, any alkylthio, any haloalkoxy, any haloalkylthio, or any alkenyl group in which the double bond can be variously substituted with $C_1$ to $C_6$ alkyl groups, aryl groups, or a combination of alkyl and aryl groups; $R^1, R^2, R^3, R^4, R^5$, and $R^6$ can be the same or different groups, and l, m and n can be any integers from 0 to 10;

(19) a compound of structure 25:

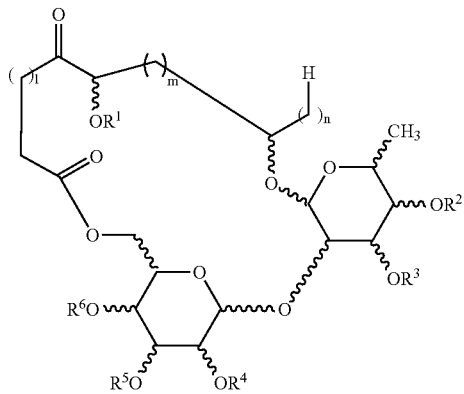

wherein $R^1$, $R^2$, $R^3$, $R^4$, $R^5$, and $R^6$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups; $R^1$, $R^2$, $R^3$, $R^4$, $R^5$, and $R^6$ can be the same or different groups, and l, m and n can be any integers from 0 to 10;

(20) a compound of structure 26:

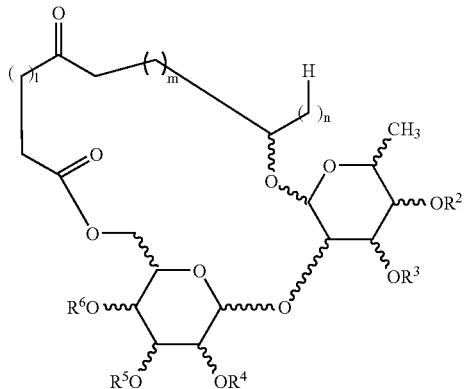

wherein $R^2$, $R^3$, $R^4$, $R^5$, and $R^6$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups; $R^2$, $R^3$, $R^4$, $R^5$, and $R^6$ can be the same or different groups, and l, m and n can be any integers from 0 to 10;

(21) a compound of structure 27:

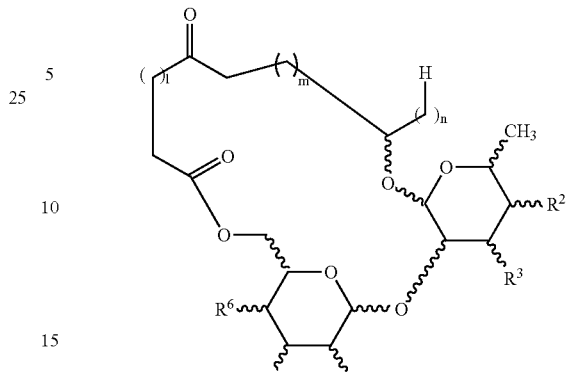

wherein $R^2$, $R^3$, $R^4$, $R^5$, and $R^6$ can variously be hydrogen or can be drawn from any alkyl group, any nitrogen-containing group, any aryl group, any alkoxy, any alkylthio, any haloalkoxy, any haloalkylthio, any alkenyl group, the groups OH, or WCOO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups; $R^2$, $R^3$, $R^4$, $R^5$, and $R^6$ can be the same or different groups, and l, m and n can be any integers from 0 to 10; and

(22) a compound of structure 28:

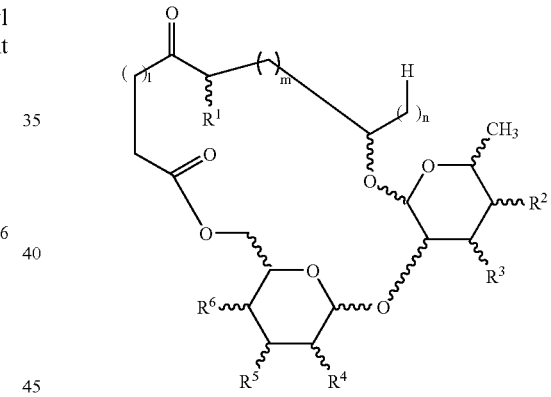

wherein $R^1$, $R^2$, $R^3$, $R^4$, $R^5$, and $R^6$ can variously be hydrogen or can be drawn from any alkyl group, any nitrogen-containing group, any aryl group, any alkoxy, any alkylthio, any haloalkoxy, any haloalkylthio, any alkenyl group, the groups OH, or WCOO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups; $R^1$, $R^2$, $R^3$, $R^4$, $R^5$, and $R^6$ can be the same or different groups, and l, m and n can be any integers from 0 to 10.

In another preferred embodiment, the invention provides a pharmaceutical composition comprising: at least one compound selected from the group consisting of structures (1), (2), (3), (4), (5), (6), (7), (14), (15), (16), (17), (18), (19), (20), (21), (22), (23), (24), (25), (26), (27), and (28), together with an emulsifying agent and alcohol, wherein the pharmaceutical composition is suitable for human drug use.

The invention provides, in a further preferred embodiment, an anticancer method comprising: administration to a human patient of a therapeutically effective amount of at least one compound selected from the group consisting of structures (1), (2), (3), (4), (5), (6), (7), (14), (15), (16), (17), (18), (19), (20), (21), (22), (23), (24), (25), (26), (27), and (28); wherein a human cancer or leukemia is treated. For example, the treated cancer may be breast cancer, ovarian cancer, lung cancer, etc.

The invention also provides, in a preferred embodiment, a method of treating a human neurodegenerative disorder, comprising: administration to a human patient of a therapeutically effective amount of at least one compound selected from the group consisting of structures (1), (2), (3), (4), (5), (6), (7), (14), (15), (16), (17), (18), (19), (20), (21), (22), (23), (24), (25), (26), (27), and (28), wherein a human neurodegenerative disorder (such as, e.g., Alzheimer's disease) is treated.

In another preferred embodiment, the invention provides a method of producing an anticancer agent, comprising at least a step of: (a) from a quantity of morning glory plant leaves, isolating an ipomoeassin compound.

Also, in a preferred embodiment, the invention provides a method of treating a human cancer or a human neurodegenerative disorder, comprising: (a) to a human patient suffering from a cancer or a neurodegenerative disorder, administering a therapeutically effective amount of an ipomoeassin compound isolated from a quantity of morning glory plant leaves, such as, e.g., inventive methods wherein a cancer is treated; inventive methods wherein a neurodegenerative disorder is treated; etc.

The invention also provides a preferred embodiment which is a method of producing an ipomoeassin compound, comprising: processing a quantity of morning glory plant material, wherein the processed plant material comprises a quantity of ipomoeassin compound having a structural formula selected from the group consisting of $C_{42}H_{58}O_{15}$, $C_{40}H_{56}O_{14}$, $C_{42}H_{58}O_{16}$, and $C_{44}H_{60}O_{17}$, and $C_{44}H_{62}O_{15}$.

DETAILED DESCRIPTION OF A PREFERRED EMBODIMENT

The invention may be appreciated with reference to the following Examples, without the invention being limited to the Examples.

Example 1

Ipomoeassins A-E, Cytotoxic Macrocyclic Glycoresins, from the Leaves of *Ipomoea squamosa* from the Suriname Rainforest The present inventors decided to re-investigate the cytotoxic constituents of *Ipomoea* sp. from Suriname after work on them had been discontinued by Bristol-Myers Squibb (BMS). The original extract which had been used by BMS\was no longer available, but eight Ipomoea extracts were available from the National Cancer Institute and two *Ipomoea* extracts were available in-house, including one (E940631) that was a re-collection of the original plant that had furnished the extract provided to BMS. Analysis of all ten extracts was carried out by LC-MS, using 280 nm as a monitoring wavelength and 800 to 1000 Dalton as a scanning range, and E940631 was chosen as the starting material since its LC-MS chromatogram showed peaks which had the same UV pattern and similar MW(s) to BMS-247181. E940631 had an $IC_{50}$ value of 8.0 μg/mL against the A2780 ovarian cancer cell line.

Experimentation

Fractionation of E940631 was carried out by flash chromatography on a C18 column followed by HPLC on C18 and then phenyl columns. Five cytotoxic compounds (1-5) were isolated, and were designated ipomoeassins A-E. Ipomoeassin D (4) showed particularly potent inhibition of the A2780 human ovarian cancer cell line with an $IC_{50}$ value of 35 nM.

Figure 1:
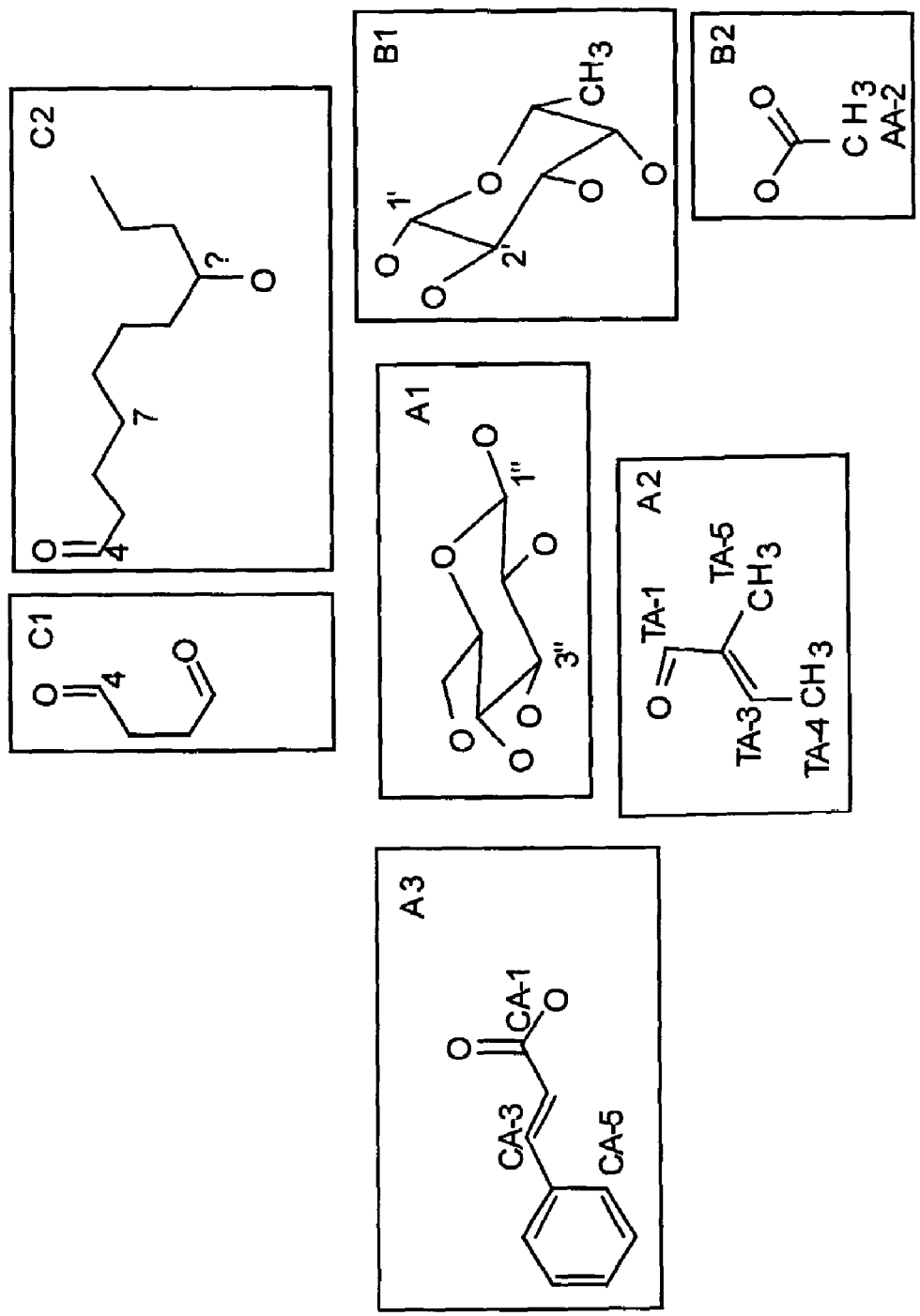
FIG. 1 shows fragments of an inventive compound of structure 1 based on 2D NMR data.

Ipomoeassin A (1) was obtained as a colorless oil, whose molecular formula was determined to be $C_{42}H_{58}O_{15}$ from the positive ion HRESINS. Its $^1H$ NMR (Table 1), $^{13}C$ NMR (Table 2), COSY, TOCSY, and ROESY data suggested the presence of glucose (fragment A1) and fucose (fragment B1) components (FIG. 1). The olefinic proton at $\delta_H$ 6.95 (1H, m, H-TA-3, TA-tiglic acid), showing HMBC correlations with both $\delta_C$ 12.1 (C-TA-5) and $\delta_C$ 168.5 (C-TA-1), had a COSY correlation with the signal at $\delta_H$ 1.23 (3H, d, J=7.1 Hz, H-TA-4). This suggested the presence of a 2-methylbut-2-enoyl moiety (fragment A2). The E stereochemistry of the double bond in fragment A2 was unequivocally assigned based on the ROESY correlations between the signal at $\delta_H$ 1.23 and the signals at $\delta_H$ 6.95 and 1.68. The deshielding of proton TA-3 due to the anisotropy of the carbonyl (C-TA-1) was also a proof for the E stereochemistry of the tigloyl residue.

FIGS. 3-11, which show $^1H$ spectra for inventive compounds of structures 1, 2, 3, 4, 5, 10, 11, 12 and 13 may be referred to regarding this Example 1.

TABLE 1

$^1H$ NMR Data (δ) for Compounds 1 to 5

| No | 1 | 2 | 3 | 4 | 5 |
|---|---|---|---|---|---|
| 2 | 2.40 ddd(17.4, 9.4, 3.4) | 2.38 ddd(17.4, 9.4, 3.4) | 2.65 ddd(17.9, 9.1, 4.2) | 2.57 ddd(18.1, 9.2, 2.8) | 2.55 ddd(18.1, 9.2, 2.8) |
|   | 2.14 ddd(17.4, 7.7, 3.5) | 2.13 ddd(17.4, 7.7, 3.5) | 1.80 ddd(17.9, 7.8, 4.4) | 2.38 ddd(18.1, 7.8, 3.4) | 2.34 ddd(18.1, 7.8, 3.4) |

TABLE 1-continued

¹H NMR Data (δ) for Compounds 1 to 5

| No | 1 | 2 | 3 | 4 | 5 |
|---|---|---|---|---|---|
| 3 | 2.65 ddd(16.1, 7.7, 3.4) | 2.62 ddd(16.1, 7.7, 3.4) | 3.01 ddd(16.4, 9.1, 4.4) | 2.83 ddd(16.3, 9.2, 3.4) | 2.81 ddd(16.3, 9.2, 3.4) |
|   | 2.52 ddd(16.1, 9.4, 3.5) | 2.50 ddd(16.1, 9.4, 3.5) | 2.21 ddd(16.4, 7.8, 4.2) | 2.43 ddd(16.3, 7.8, 2.8) | 2.39 ddd(16.3, 7.8, 2.8) |
| 5 | 2.07 t(6.0) | 2.07 t(6.2) | 3.96 m | 5.05 dd(6.2, 3.9) | 5.04 dd(6.2, 3.9) |
| 6 | 1.56 m, 1.65 m | 1.56 m, 1.65 m | 1.80 m | 1.75 m, 1.95 m | 1.75 m, 1.95 m |
| 7 | 1.32 m | 1.31 m | 1.45 m | 1.50 m | 1.50 m |
| 8 | 1.34 m | 1.29 m | 1.35 m | 1.30 m | 1.30 m |
| 9 | 1.35 m, 1.55 m | 1.35 m, 1.51 m | 1.45 m | 1.50 m | 1.50 m |
| 10 | 1.54 m, 1.72 m | 1.52 m, 1.70 m | 1.50 m, 1.70 m | 1.50 m, 1.70 m | 1.50 m, 1.70 m |
| 11 | 3.72$^a$ m | 3.71 m | 3.66$^c$ m | 3.70 m | 3.71 m |
| 12 | 1.54 m, 1.65 m | 1.53 m, 1.61 m | 1.65 m | 1.55 m, 1.65 m | 1.55 m, 1.65 m |
| 13 | 1.55 m | 1.57 m | 1.55 m | 1.55 m | 1.55 m |
| 14 | 0.95 t(7.1) | 0.96 t(7.1) | 0.96 t(6.9) | 0.95 t(7.1) | 0.97 t(6.9) |
| 1' | 4.40 d(7.7) | 4.38 d(7.6) | 4.32 d(7.6) | 4.29 d(7.6) | 4.28 d(7.6) |
| 2' | 3.96$^b$ dd(9.5, 7.7) | 3.88 dd(9.5, 7.6) | 3.90 dd(9.7, 7.6) | 3.88 dd(9.5, 7.6) | 3.80$^e$ dd(9.5, 7.6) |
| 3' | 3.72$^a$ dd(9.5, 3.7) | 3.65 dd(9.5, 3.3) | 3.66$^c$ dd(9.7, 3.4) | 3.62 dd(9.5, 3.7) | 3.55 dd(9.5, 3.7) |
| 4' | 5.15 dd(3.7, 0.5) | 3.53 br s | 5.12 br d(3.4) | 5.09 br d(3.7) | 3.44 br s |
| 5' | 3.10 qd(6.4, 0.5) | 3.11 br q(6.4) | 3.11 br q(6.4) | 3.06 br q(6.4) | 3.02 br q(6.4) |
| 6' | 1.10 d(6.4) | 1.29 d(6.4) | 1.09 d(6.4) | 1.25 d(6.4) | 1.25 d(6.4) |
| 1" | 4.52 d(7.9) | 4.59 d(7.8) | 4.54 d(7.8) | 4.51$^d$ d(7.8) | 4.50$^f$ d(7.8) |
| 2" | 3.91$^b$ dd(9.7, 7.9) | 3.95 dd(9.7, 7.8) | 3.83 dd(9.7, 7.8) | 3.79 dd(9.7, 7.8) | 3.81$^e$ dd(9.7, 7.8) |
| 3" | 5.39 t(9.7) | 5.50 t(9.7) | 5.41 t(9.7) | 5.39 t(9.7) | 5.38 t(9.7) |
| 4" | 5.69 t(9.7) | 5.72 t(9.7) | 5.72 t(9.7) | 5.69 t(9.7) | 5.70 t(9.7) |
| 5" | 3.24 ddd(9.7, 3.2, 1.6) | 3.44 br d(9.7) | 3.26 br d(9.7) | 3.29 br d(9.7) | 3.36 br d(9.7) |
| 6" | 4.66 dd(12.6, 3.2) | 4.66 dd(12.6, 2.1) | 4.37 dd(12.4, 1.6) | 4.51$^d$ br d(11.5) | 4.51$^f$ dd(11.0, 2.0) |
|   | 4.11 dd(12.6, 1.6) | 4.16 br d(12.6) | 4.26 dd(12.4, 0.9) | 4.19 br d(11.5) | 4.20 br d(11.0) |
| AA-2 | 1.82 s | | 1.84 s | 1.82 s | |
| AA-2' | | | | 1.70 s | 1.67 br s |
| TA-3 | 6.95 m | 6.95 m | 6.95 m | 6.95 m | 6.95 m |
| TA-4 | 1.23 d(7.1) | 1.27(7.1) | 1.27 d(7.1) | 1.26 d(7.1) | 1.25 d(7.1) |
| TA-5 | 1.68 br s | 1.72 br s | 1.71 br s | 1.70 br s | 1.67 br s |
| CA-2 | 6.39 d(15.9) | 6.40 d(16.1) | 6.38 d(16.0) | 6.37 d(15.8) | 6.40 d(16.1) |
| CA-3 | 7.81 d(15.9) | 7.81 d(16.1) | 7.81 d(16.0) | 7.81 d(15.8) | 7.81 d(16.1) |
| CA-5 | 6.89-7.07 | 6.88-7.07 | 6.88-7.03 | 6.88-7.03 | 6.88-7.03 |
| CA-6 | 6.89-7.07 | 6.88-7.07 | 6.88-7.03 | 6.88-7.03 | 6.88-7.03 |
| CA-7 | 6.89-7.07 | 6.88-7.07 | 6.88-7.03 | 6.88-7.03 | 6.88-7.03 |

AA = acetoyl;
TA = tigloyl;
CA = cinnamoyl;
$^{a-f}$interchangable.

TABLE 2

¹³C NMR Data (δ) for Compounds 1 to 5

| No$^a$ | 1 | 2 | 3 | 4 | 5 |
|---|---|---|---|---|---|
| 1 | 171.5 | 171.5 | 171.6 | 171.3 | 171.4 |
| 2 | 37.3$^b$ | 37.4 | 33.0 | 34.0$^l$ | 34.0$^r$ |
| 3 | 29.7$^c$ | 29.5$^f$ | 28.3 | 28.3 | 28.3 |
| 4 | 208.4 | 208.3 | 210.7 | 205.7 | 205.8 |
| 5 | 41.6 | 41.5 | 76.3$^i$ | 78.4$^m$ | 78.2$^s$ |
| 6 | 23.8 | 23.6 | 32.7 | 30.3$^m$ | 30.3$^t$ |
| 7 | 28.7 | 28.6 | 22.7 | 24.0 | 24.0 |
| 8 | 29.4$^c$ | 29.3$^f$ | 29.9 | 30.6$^n$ | 30.5$^t$ |
| 9 | 25.5 | 25.4 | 25.1 | 25.2 | 25.2 |
| 1 | 34.3 | 34.3 | 34.1 | 34.0$^l$ | 34.0$^r$ |
| 11 | 79.0 | 78.8 | 78.8 | 78.5$^m$ | 78.5$^s$ |
| 12 | 37.6$^b$ | 37.4 | 37.6 | 37.7 | 37.7 |
| 13 | 18.7 | 18.8 | 18.8 | 18.9 | 18.9 |
| 14 | 14.4$^d$ | 14.3$^g$ | 14.4$^j$ | 14.4$^o$ | 14.4$^u$ |
| 1' | 100.8 | 100.6 | 100.7 | 100.6 | 100.5 |
| 2' | 84.0 | 83.7 | 83.9 | 83.9 | 84.2 |
| 3' | 72.7$^e$ | 74.2$^h$ | 72.7$^k$ | 72.8$^p$ | 74.0 |
| 4' | 72.9$^e$ | 71.6 | 72.6$^k$ | 72.7$^p$ | 71.6 |
| 5' | 69.0 | 70.2 | 68.9 | 68.9 | 70.0 |
| 6' | 14.1$^d$ | 14.0$^g$ | 14.1$^j$ | 14.1$^o$ | 14.1$^u$ |
| 1" | 106.6 | 106.4 | 106.4 | 106.6 | 106.7 |
| 2" | 74.8 | 74.6$^h$ | 74.7 | 75.0 | 74.9 |
| 3" | 6.4 | 76.3 | 76.4$^i$ | 76.6 | 76.6 |
| 4" | 67.8 | 67.8 | 67.9 | 67.6 | 67.7 |
| 5" | 73.0$^e$ | 73.0 | 72.8$^k$ | 72.9$^p$ | 72.9 |
| 6" | 61.5 | 61.4 | 61.6 | 61.2 | 61.2 |
| AA-1 | 171.0 | | | 171.0 | 170.9 |
| AA-2 | 20.5 | | | 20.5 | 20.4$^q$ |
| AA-1' | | | | 169.8 | 169.8 |
| AA-2' | | | | 20.3$^q$ | 20.3 |
| TA-1 | 168.5 | 168.5 | 168.5 | 168.8 | 168.9 |
| TA-2 | 128.0 | 128.0 | 128.0 | 128.0 | 128.0 |
| TA-3 | 139.2 | 139.1 | 139.3 | 139.4 | 139.6 |
| TA-4 | 16.6 | 16.6 | 16.5 | 16.5 | 16.6 |
| TA-5 | 12.1 | 12.0 | 12.1 | 12.0 | 12.0 |
| CA-1 | 165.6 | 165.5 | 165.4 | 165.5 | 165.5 |
| CA-2 | 117.6 | 117.6 | 117.5 | 117.6 | 117.5 |
| CA-3 | 146.1 | 146.0 | 146.2 | 146.2 | 146.2 |
| CA-4 | 134.5 | 134.4 | 134.4 | 134.4 | 134.4 |
| CA-5 | 128.5 | 128.4 | 128.5 | 128.4 | 128.3 |
| CA-6 | 128.9 | 128.8 | 128.9 | 128.8 | 128.5 |
| CA-7 | 130.4 | 130.3 | 130.4 | 130.4 | 130.4 |

$^a$AA = acetyl; TA = tigloyl; CA = cinnamoyl.
$^{b-u}$interchangable.

Structures 1-7, 14

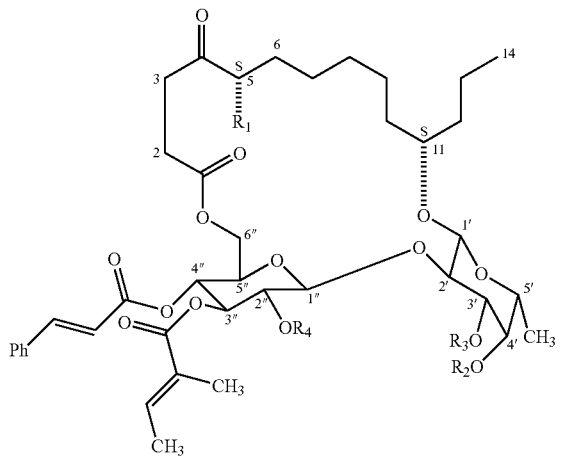

1  $R_1 = R_3 = R_4 = H; R_2 = Ac;$
2  $R_1 = R_2 = R_3 = R_4 = H$
3  $R_1 = OH; R_2 = Ac; R_3 = R_4 = H$
4  $R_1 = OAc; R_2 = Ac; R_3 = R_4 = H$
5  $R_1 = OAc; R_2 = R_3 = R_4 = H$
6  $R_1 = H; R_2 = R_3 = R_4 = Ac$
7  $R_1 = OAc; R_2 = R_3 = R_4 = Ac$

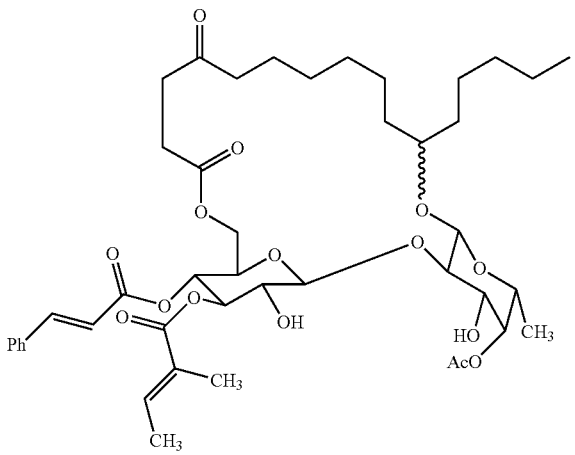

14

The conventions followed in notating bonds throughout this application are as follows. When the stereochemistry of a chiral center is designated herein by a hatched bond (┈┈) that bond is considered to be below the plane of the main chain. If the stereochemistry of a bond is designated by a solid bond (—) then that bond is considered to be above the plane of the main chain as written. If the stereochemistry of a bond is designated by a wavy bond (∼∼) then that bond is considered to be either above or below the plane of the main chain as written.

A pair of trans-coupled olefinic protons at $\delta_H$ 7.81 (1H, d, J=15.9 Hz) and 6.39 (1H, d, J=15.9 Hz), and a multiplet due to 5 protons at $\delta_H$ 6.89-7.07 suggested the presence of a 3-phenylprop-2-enoyl moiety (CA-cinnamic acid, fragment A3). This was confirmed by the HMBC correlations between $\delta_H$ 7.81 and $\delta_C$ 134.5 (C-CA-4) and 128.5 (C-CA-5). The methyl singlet at $\delta_H$ 1.82 (3H, s) showed an HMBC correlation with the carbonyl at $\delta_C$ 171.0 (C-AA-1, AA-acetic acid) suggesting the presence of an acetyl moiety (fragment B2). The $^1$H NMR spectrum of 1 also exhibited signals for two methylenes at $\delta_H$ 2.65 (H-3a) and 2.52 (H-3b), 2.40 (H-2a) and 2.14 (H-2b). These two methylenes were flanked by two carbonyls and displayed one spin system (fragment C1) in the TOCSY spectrum. The methyl triplet at $\delta_H$ 0.95 (3H, t, J=7.1 Hz, H-14), the methylene triplet at $\delta_H$ 2.07 (2H, t, J=6.0 Hz, H-5), the oxygenated methine at $\delta_H$ 3.72 (1H, m, H-11), and the other seven methylenes, all of which were parts of another spin system (fragment C2), were separated from fragment C1 by the carbonyl group at C-4 ($\delta_C$ 208.4), since C-4 showed HMBC correlations with H-2, H-3, and H-5.

Figure 2:
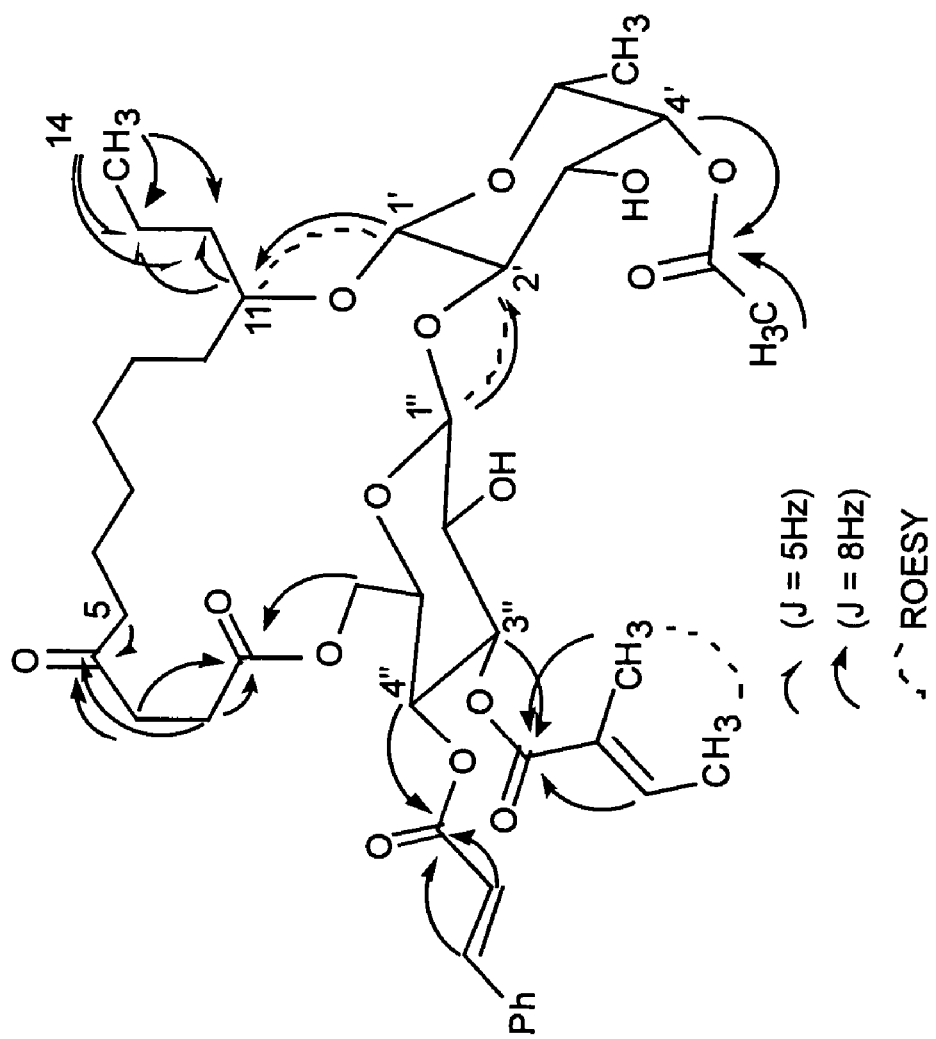
FIG. 2 shows key HMBC and ROESY correlations of structure 1.
Figure 3:
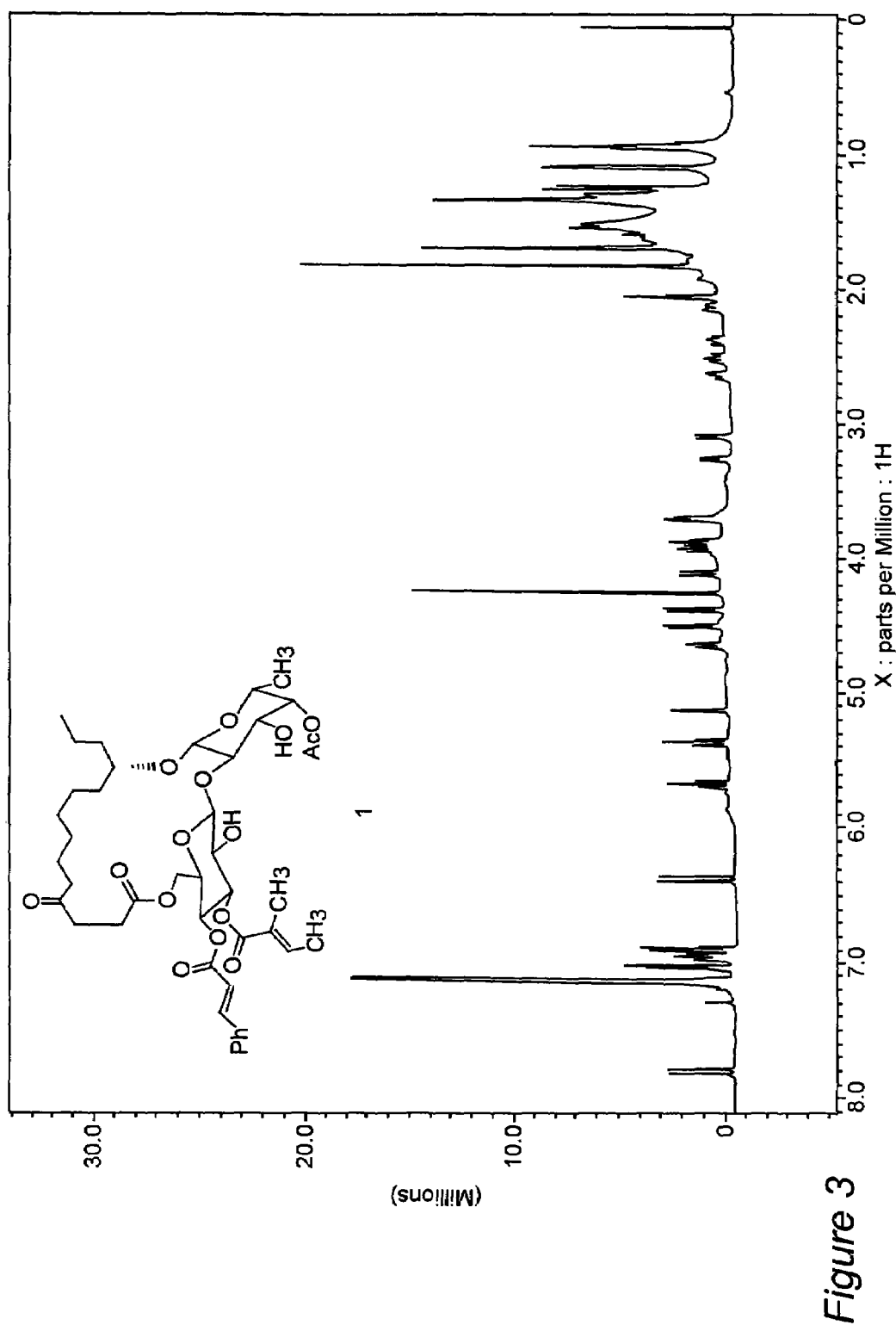
FIG. 3 shows $^1H$ spectra for an inventive compound of structure 1.
Figure 4:
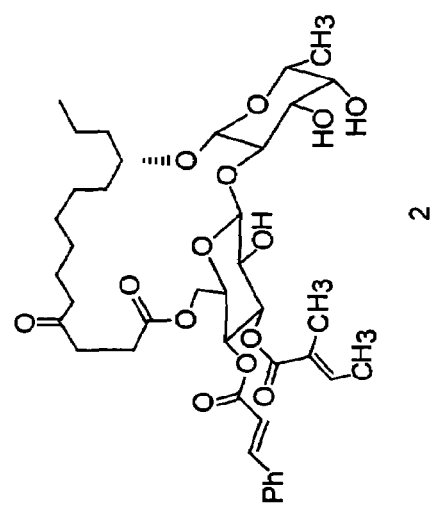
FIG. 4 shows $^1H$ spectra for an inventive compound of structure 2.
Figure 4:
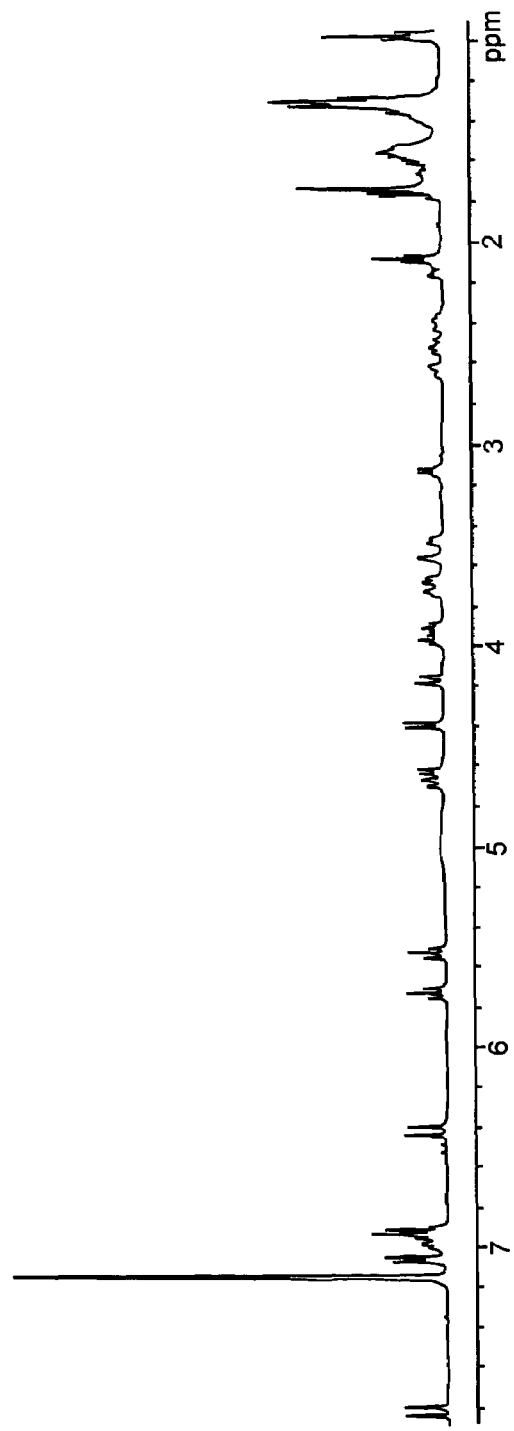
Figure 5:
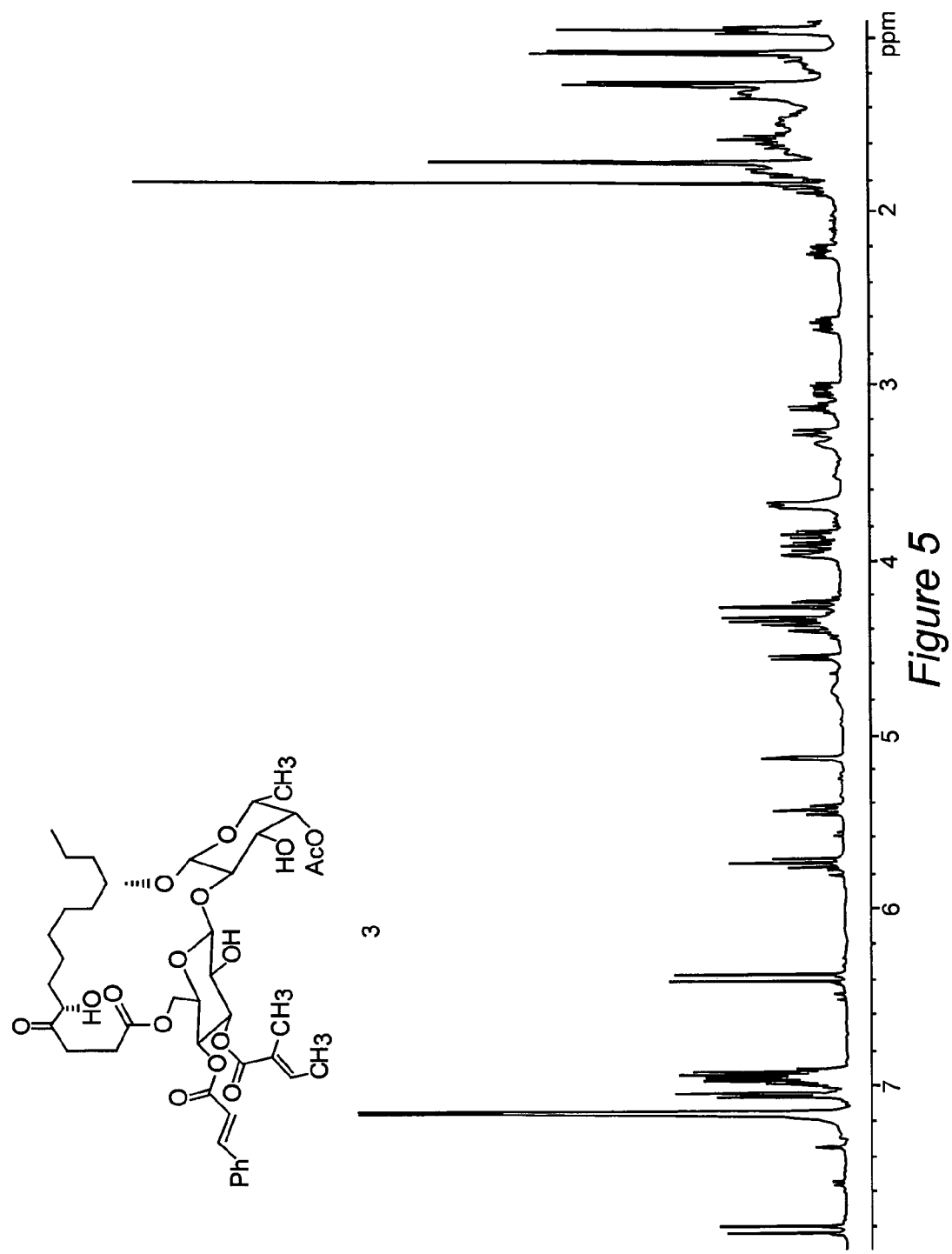
FIG. 5 shows $^1H$ spectra for an inventive compound of structure 3.
Figure 6:
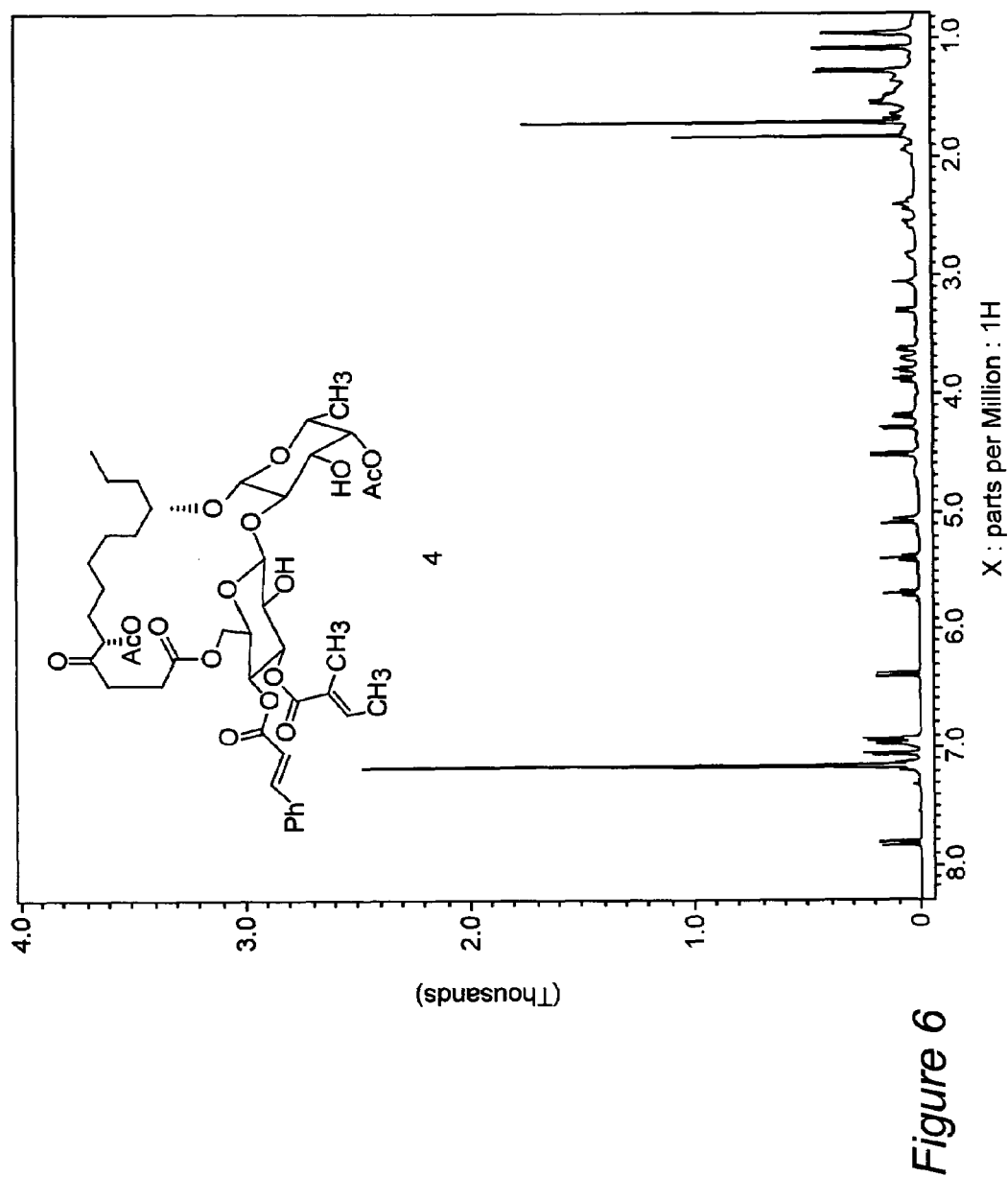
FIG. 6 shows $^1H$ spectra for an inventive compound of structure 4.
Figure 7:
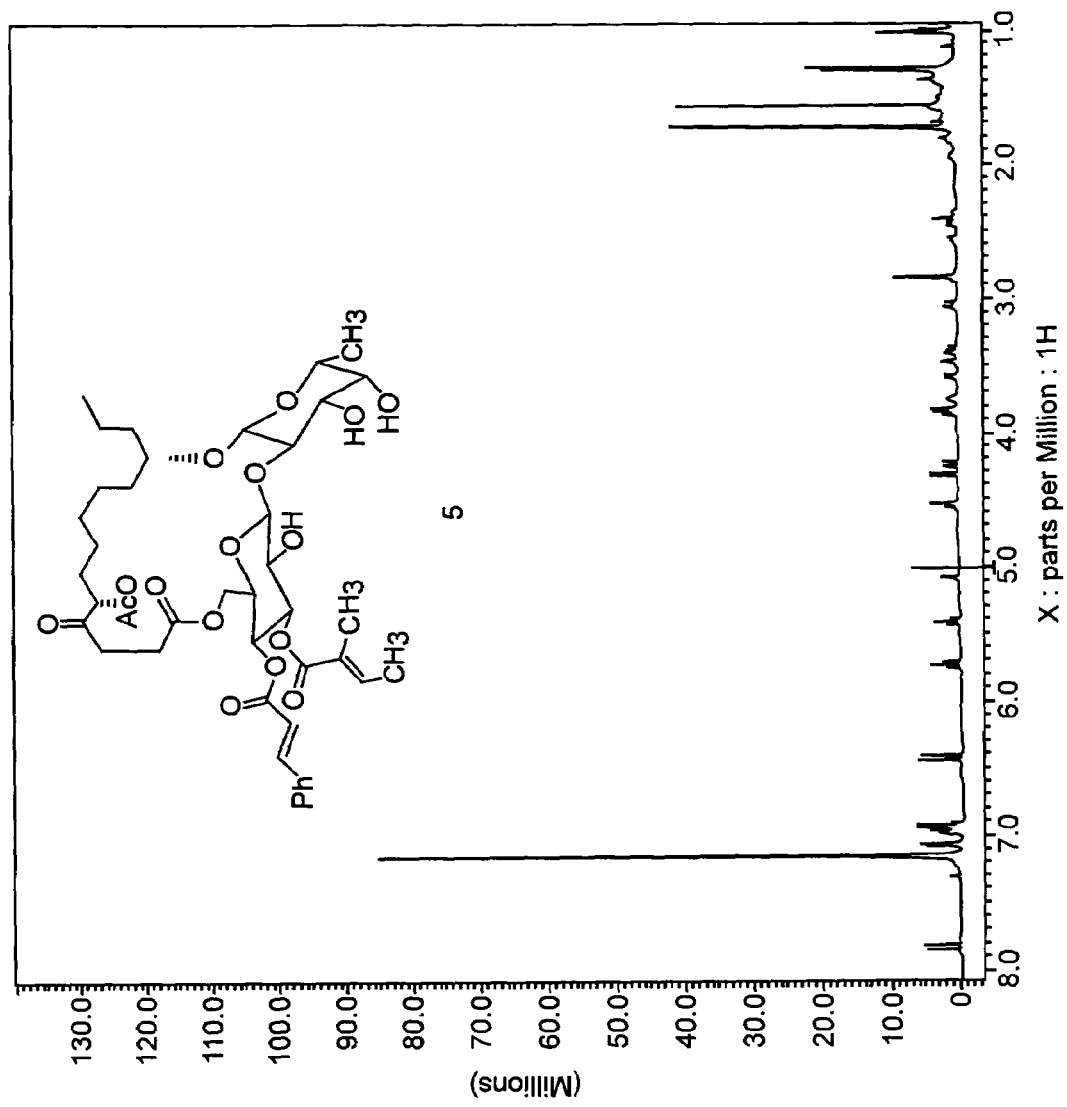
FIG. 7 shows $^1H$ spectra for an inventive compound of structure 5.
Figure 8:
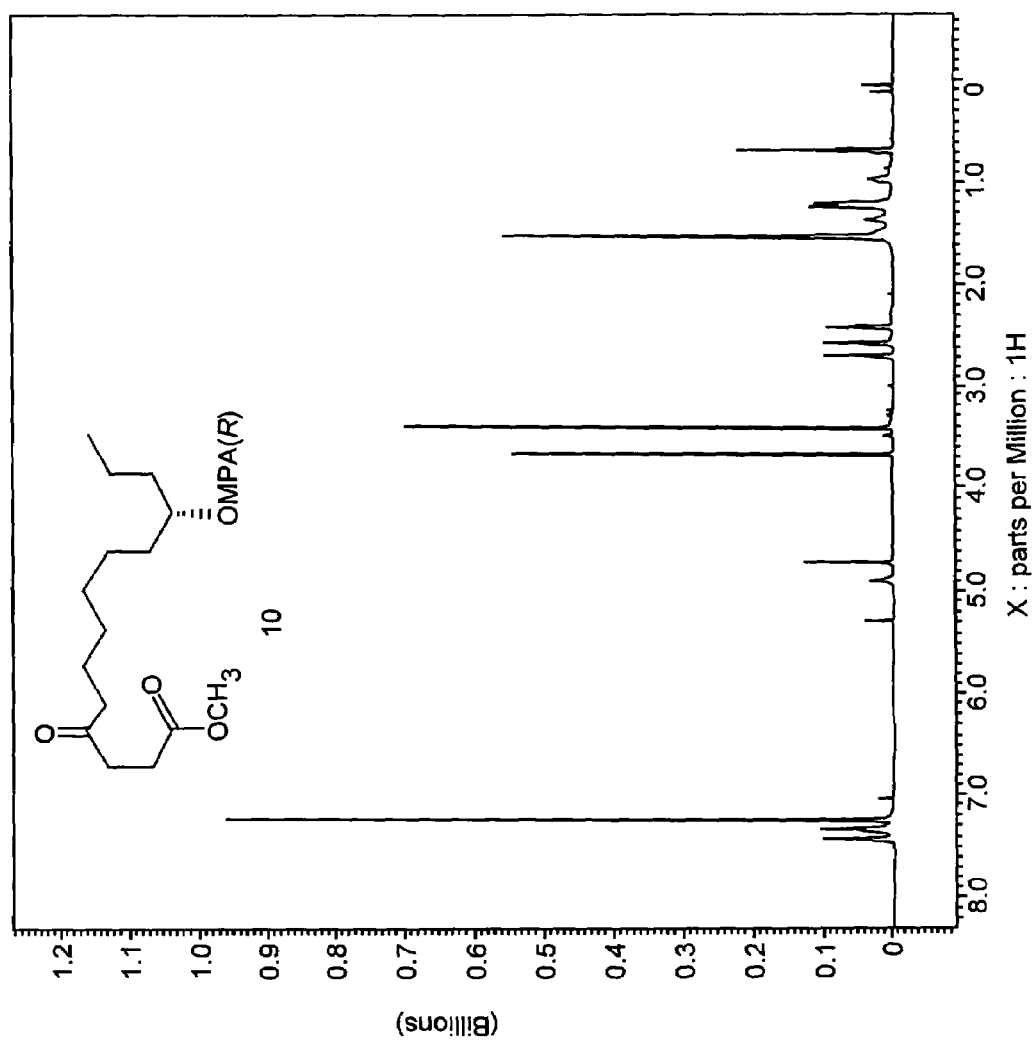
FIG. 8 shows $^1H$ spectra for an inventive compound of structure 10.
Figure 9:
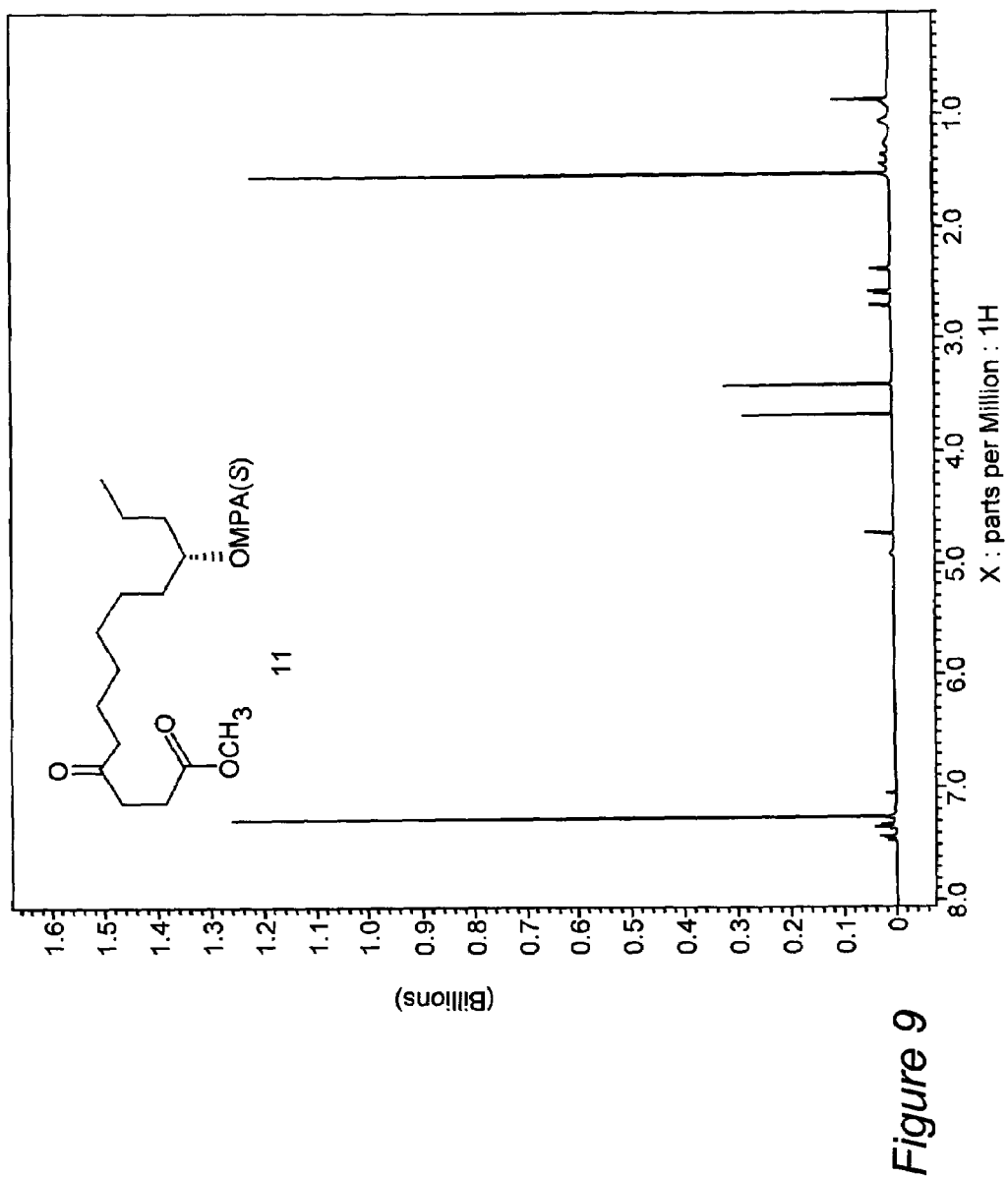
FIG. 9 shows $^1H$ spectra for an inventive compound of structure 11.
Figure 10:
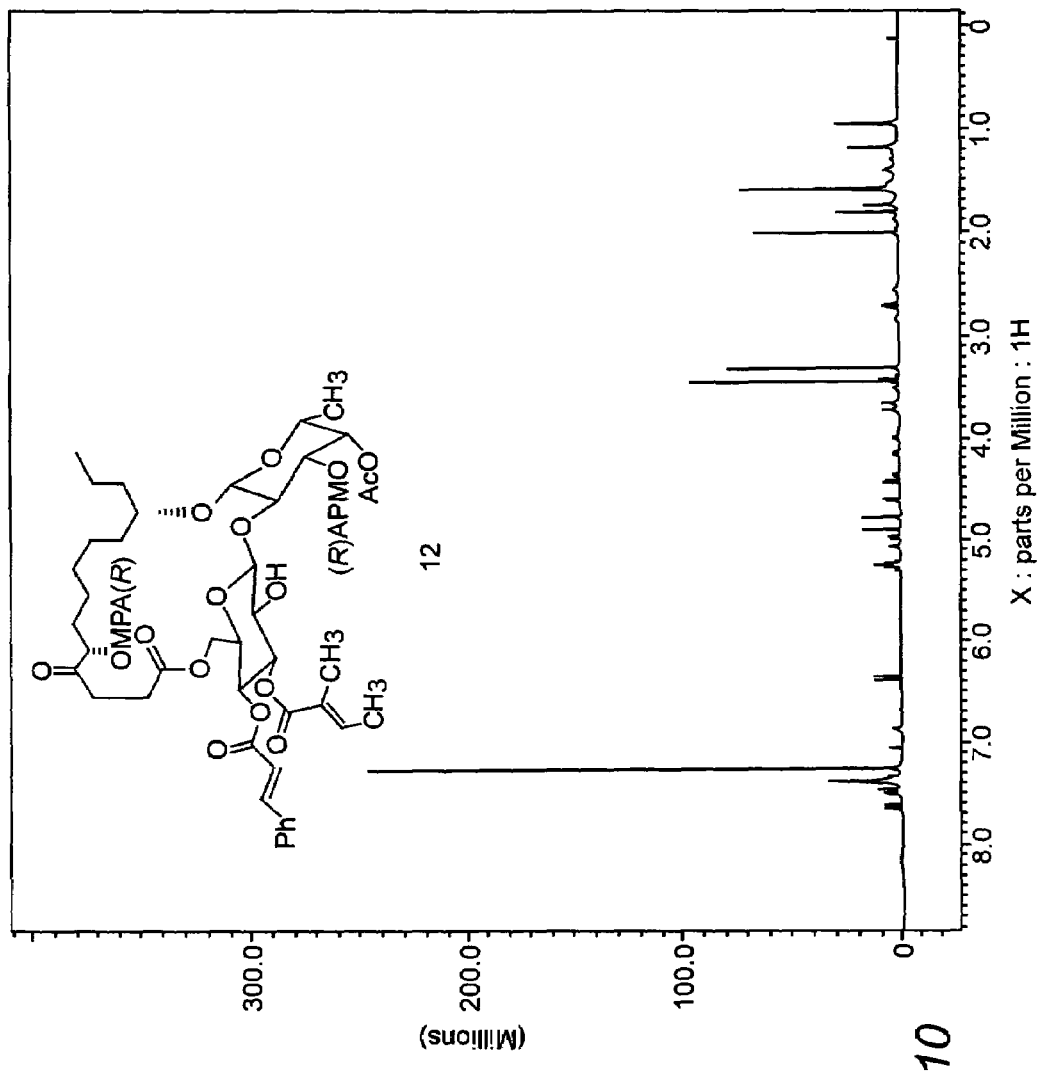
FIG. 10 shows $^1H$ spectra for an inventive compound of structure 12.
Figure 11:
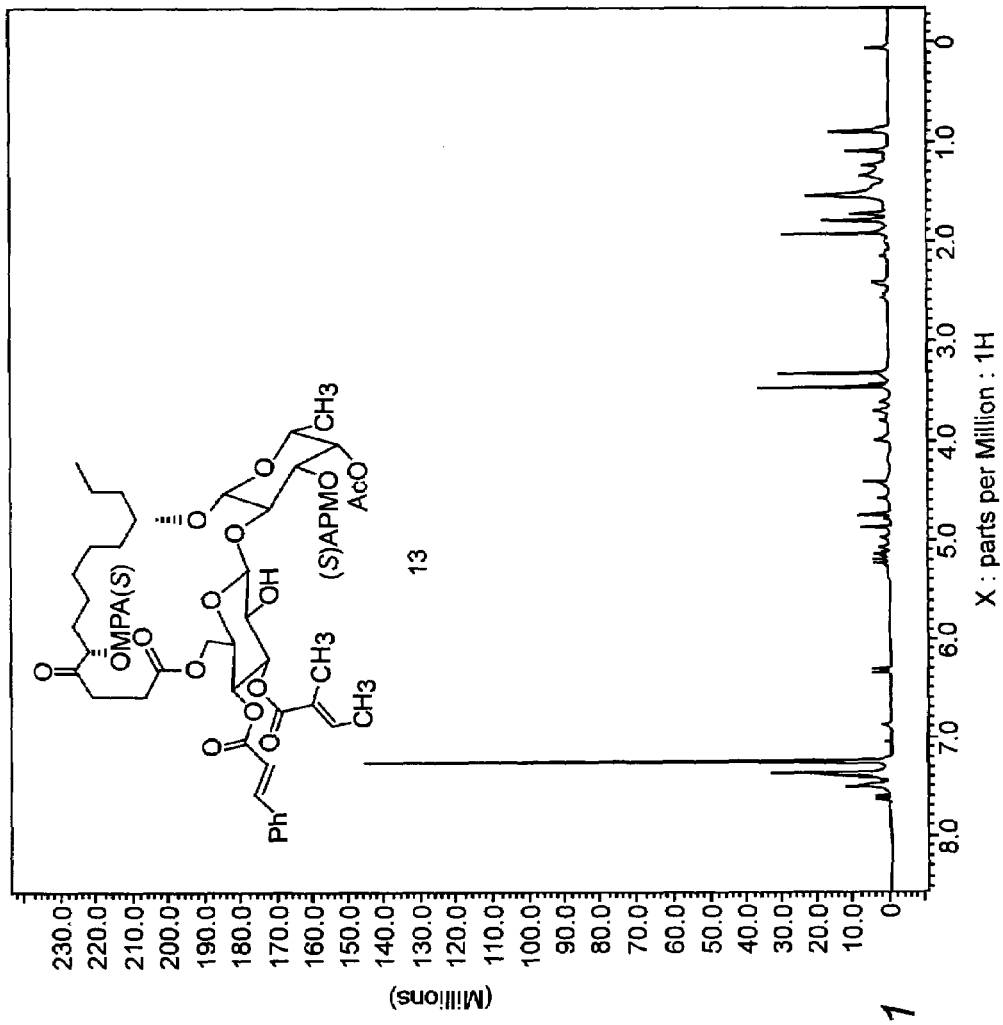
FIG. 11 shows $^1H$ spectra for an inventive compound of structure 13.
Figure 12A:
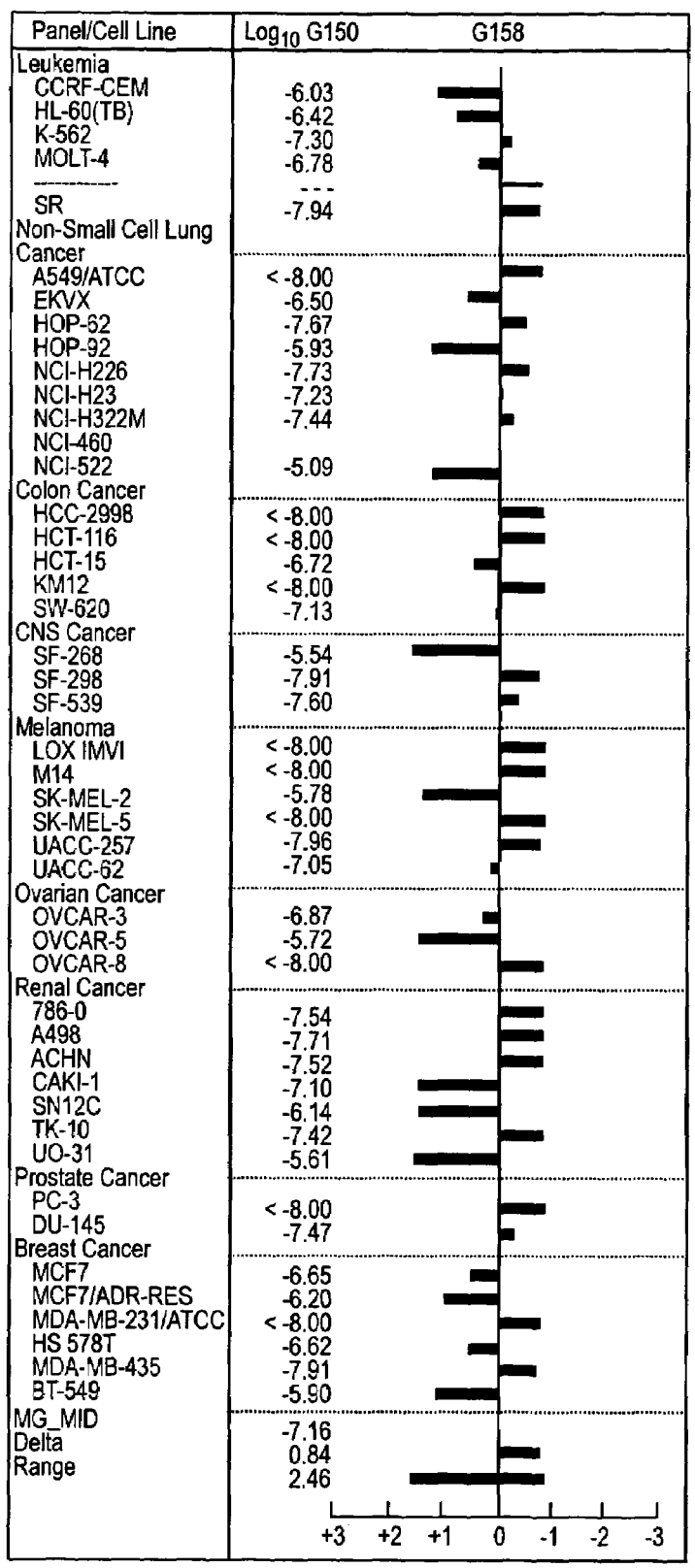
FIG. 12 shows experimental data for the 60-cell line National Cancer Institute (NCI) tests, testing an inventive compound of structure 1.
Figure 12B:
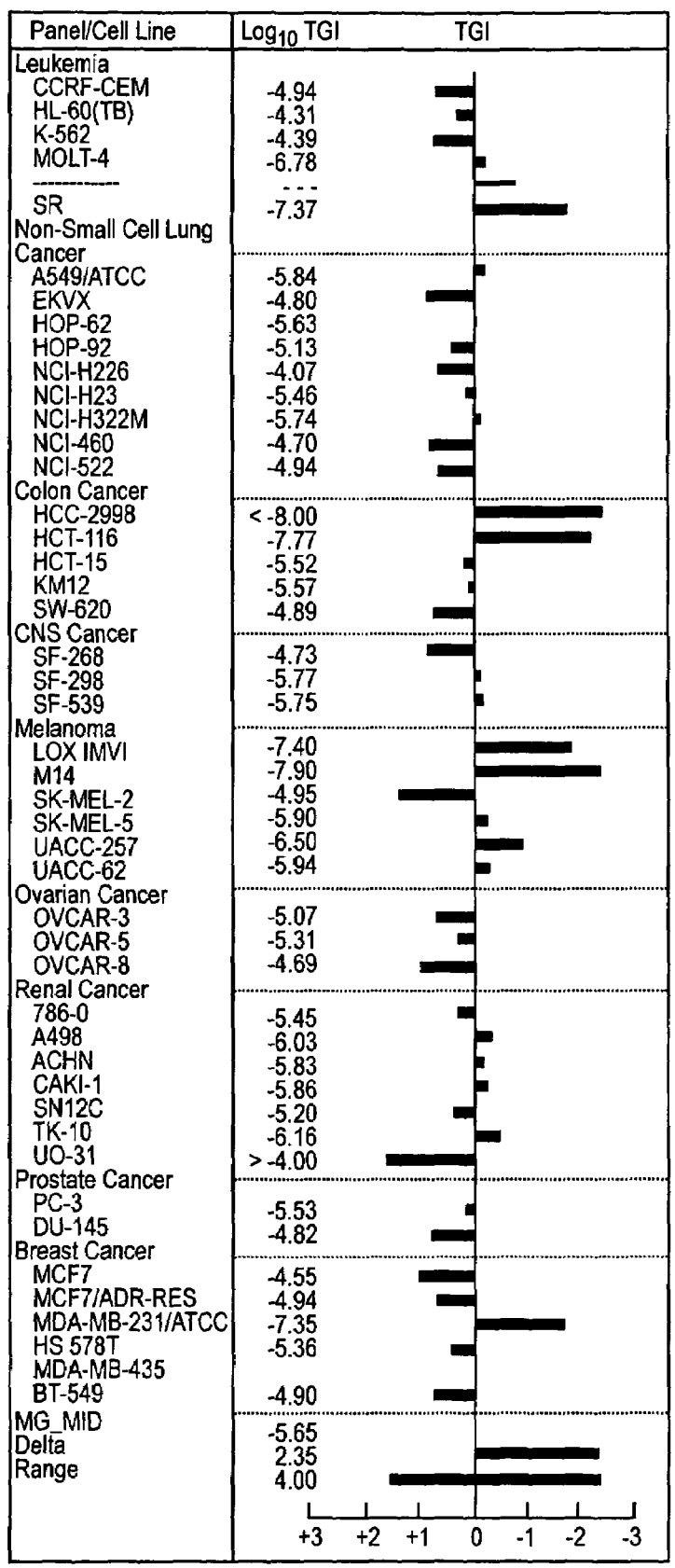
Figure 12C:
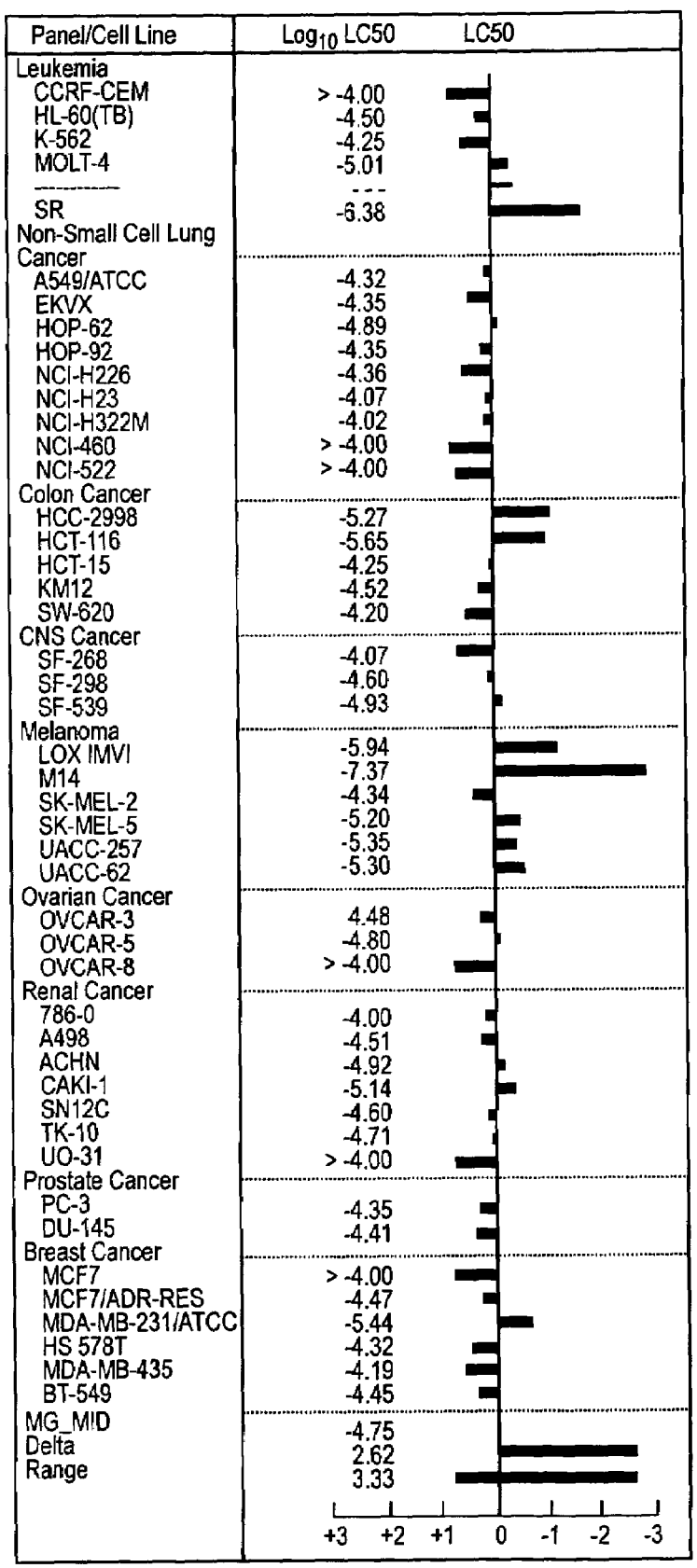

The HMBC (FIG. 2) experiment also provided evidence for the location of the ester substituents. The methyl group at $\delta_H$ 1.82 (H-AA-2) and H-4' ($\delta_H$ 5.15, H-F-4, F: fucose) both correlated with the carbonyl at $\delta_C$ 171.0 (C-AA-1) in the HMBC spectrum. The carbonyl group at $\delta_C$ 168.5 was assigned to carbon TA-1 based on its HMBC correlations with H-3" ($\delta_H$ 5.39, H-G-3, G: glucose), proton TA-5 ($\delta_H$ 1.68), and proton TA-3 ($\delta_H$ 6.95); these correlations established the acylation position of the tigloyl group as 3" (C-G-3). $^{13}$C—$^1$H long-range cross peaks were observed between the carbonyl group at $\delta_C$ 165.6 (C-CA-1) and H-4" ($\delta_H$ 5.69, H-G-4), proton CA-2 ($\delta_H$ 6.39), and proton CA-3 ($\delta_H$ 7.81), which confirmed the presence of the cinnamoyl moiety at the 4"-position (C-G-4). The site of lactonization ($\delta_C$ 171.5, C-1) was determined to be at C-6" (C-G-6) of the glucose by the observed $^2$J coupling with H$_2$-2 ($\delta_H$ 2.40 and 2.14) and $^3$J couplings with H$_2$-3 ($\delta_H$ 2.65 and 2.52) and H$_2$-6" ($\delta_H$ 4.66, 4.11, H$_2$-G-6).

In the HMBC spectrum of 1, H-1" ($\delta_H$ 4.52, H-G-1, G: glucose) showed a $^3$J correlation with C-2' ($\delta_C$ 84.0, C—F-2, F: fucose), which established the connectivity between fucose and glucose. A $^3$J CH interaction between H-1' ($\delta_H$ 4.40, H—F-1) and the oxygenated carbon ($\delta_C$ 79.0, C-11) on fragment C2 was observed. Both H$_3$-14 and H-11 showed HMBC (J$_{CH}$=5 Hz) correlations with C-12 and C-13, which meant that the oxygenated methine had to be located at position 11. These correlations established the structure of 1.

In order to determine the stereochemistry at the 11-position, 1 was hydrolyzed first with base and then with acid to yield 11-hydroxy-4-oxo-tetradecanoic acid (8). The long chain fatty acid (8) was reacted with excess diazomethane to furnish 11-hydroxy-4-oxo-tetradecanoic acid methyl ester (9). Compound 9 was converted to the two Mosher esters 10 and 11 with (R)- and (S)-methoxyphenylacetic acid (MPA), using the EDCI/DMAP coupling conditions. (Seco, J. M.; Quinoa, E.; Riguera, R., *Tetrahedron: Asymmetry* 2001, 12, 2915-2925.) The resulting 11-MPA esters 10 and 11 were subjected to NMR analysis. The chemical shift differences $\Delta\delta^{RS}$ were significant (Scheme 1), which made it possible to conclude that 1 had the (S)-configuration at C-11. The sugars were determined as D-glucose and D-fucose by hydrolysis and determination of the sign of rotation of the isolated carbohydrates. This conclusion was supported by MM2 calculations, which indicated that only the diastereomer with both D-sugars would give the relatively strong ROESY correlations between H-11 and H—F-1 and between H—F-2 and H-G-1 that were exhibited in the spectrum of 1.

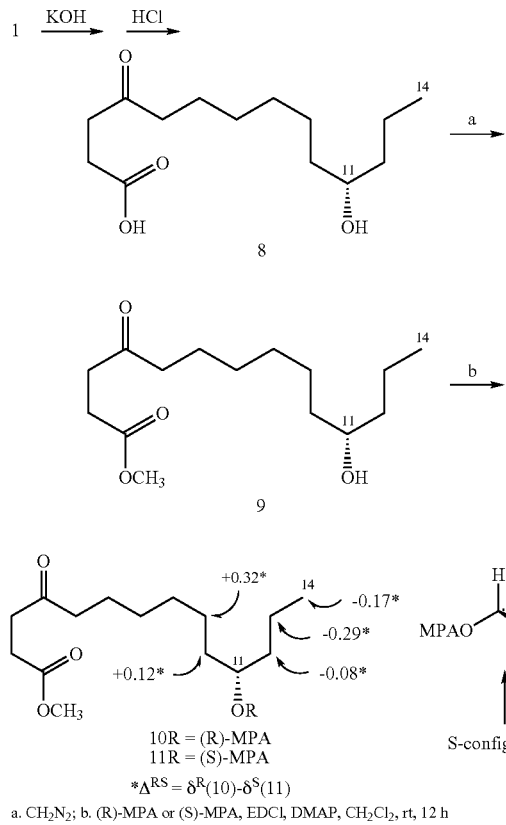

Scheme 1 a. $CH_2N_2$; b. (R)-MPA or (S)-MPA, EDCl, DMAP, $CH_2Cl_2$, rt, 12 h

Ipomoeassin B (2) was also obtained as a colorless oil, and the molecular formula $C_{40}H_{56}O_{14}$ was determined by HRFABMS and $^{13}C$ NMR. A careful analysis of its UV, IR, MS, 1D NMR (Tables 1 and 2) and 2D NMR data resulted in the conclusion that the structure of 2 was similar to that of 1. It was hypothesized that the only difference between these two compounds was the presence of a hydroxyl group, rather than an acetoxyl group, located at the 4'-position in 2. This was confirmed by the acetylation of both 1 and 2 to the same product 6. The detailed assignments of the $^1H$ NMR and $^{13}C$ NMR signals were performed by COSY, TOCSY, ROESY, HMQC and HMBC experiments. Accordingly, the structure of 2 was established as shown.

Ipomoeasssin C (3) was isolated as a colorless oil, and its molecular formula was established as $C_{42}H_{58}O_{16}$ by HRFABMS. The $^1H$ NMR (Table 1), $^{13}C$ NMR (Table 2), COSY, TOCSY, and ROESY data of 3 also showed the presence a fucose, a glucose, a tiglic acid, a cinnamic acid, an acetic acid, and a long chain fatty acid. These spectra indicated that 3 was also closely related to 1, but contained a resonance for a secondary alcohol ($\delta_H$ 3.96/$\delta_C$ 76.3 ppm) instead of a methylene group of 1 ($\delta_H$ 2.07/$\delta_C$ 41.6 ppm). Based on its COSY, TOCSY, ROESY, HMQC and HMBC spectra, 3 was determined to be the 5-hydroxy derivative of 1. The absolute stereochemistry of the 5-position of 3 was also determined as S by analysis of the $^1H$ NMR spectra of the Mosher esters 12 and 13 (Scheme 2). The stereochemistry at the 11-position and of the fucose and glucose moieties could not be determined experimentally because of the limited sample size. It is probable however that these stereochemistries are the same as those of ipomoeassin A (1) because the compounds almost certainly share the same biosynthetic pathway. Compound 3 exhibited the same positive direction of optical rotation as 1, which supported the above assumption. The structure of ipomoeassin C is thus assigned as 3.

Scheme 2

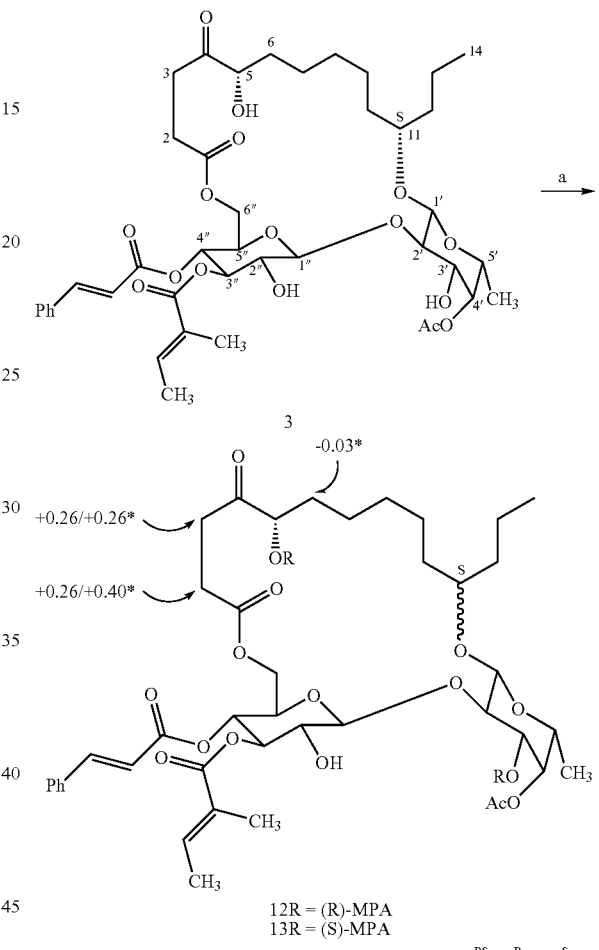

Key: (a) (R)-MPA or (S)-MPA, EDCl, DMAP, $CH_2Cl_2$, rt, 12 h *Ad$^{RS}$ = d$^R$(12)-d$^S$(13)

The molecular formula of ipomoeassin D (4) was established as $C_{44}H_{60}O_{17}$ by HRFABMS. The $^1H$ NMR and $^{13}C$ NMR spectra of 4 were very similar to those of 3 (Tables 1 and 2). The major difference between 3 and 4 was the presence of an extra acetate group (C=O: $\delta_C$ 169.8; $CH_3$: $\delta_H$ 1.70/$\delta_C$ 20.3) at the 5-position in 4, which resulted in chemical shift changes in the $^1H$ NMR spectra for H-5 from $\delta_H$ 3.96 (3) to $\delta_H$ 5.05 (4), and in the $^{13}C$ NMR spectrum for C-5 from $\delta_C$ 76.3 (3) to $\delta_C$ 78.4 (4). The structure and stereochemistry of 4 were confirmed by acetylation of both 3 and 4 separately to produce the same acetylated derivative 7, thus confirming that both 3 and 4 have the S-configuration at the 5-position.

Ipomoeassin E (5) was also obtained as a colorless oil, and its molecular formula of $C_{42}H_{58}O_{16}$ was determined by HRFABMS and $^{13}C$ NMR. The $^1H$ NMR spectrum of 5 was similar to that of 3, with the only difference being the position of substitution of the acetyl group. In the HMBC spectrum of 5, H-2, H-3, and H-5 correlated to C-4, and both H-5 ($\delta_H$ 5.04, dd, J=6.2, 3.9 Hz) and H-AA-2' ($\delta_H$ 1.67, s) showed HMBC correlations to the carbonyl group at $\delta_C$ 169.8 (C-AA-1'), which suggested that the acetoxyl group was located at C-5 in 5 instead of C-4' as in 3. The detailed assignments of the $^1$H NMR and $^{13}$C NMR signals were performed by COSY, TOCSY, ROESY, HSQC and HMBC experiments. Acetylation of 5 gave 7, which confirmed the structure of ipomoeassin E (5) and indicated that it had the same stereochemistry as 3 and 4 at the 5-position.

Ipomoeassin F (14) was also obtained as a colorless oil, and its $^1$H NMR spectrum was nearly identical to that of ipomoeassin A (1). The apparent difference between their $^{13}$C NMR spectra was located at high field (10 to 50 ppm), therefore it was deduced that compound 1 had a C16 chain rather than a C14, with two more CH$_2$ groups than 1. The chemical shifts of C-1 to C-6 were close to those of 1, and C-7 to C-16 to 11-hydroxyhexadecanoic acid, which confirmed the above deduction. The spin systems of 1 were determined from COSY and TOCSY spectra. The connectivities from C-11 to H-1 of fucose, C-2 of fucose to H-1 of glucose, H$_2$-6 of glucose to C-1 of the long chain, acetyl to C-4 of fucose, tigloyl and E-cinnamoyl to C-3 and C-4 of glucose, were established from HMQC and HMBC spectra. The configurations at position-11 and the sugar moieties were determined by analysis of its ROESY spectrum.

All the ipomoeassins showed cytotoxicity towards the A2780 ovarian cancer cell line. (Louie, K. G.; Behrens, B. C.; Kinsella, T. J.; Hamilton, T. C.; Grotzinger, K. R.; McKoy, W. M., Winker, M. A.; Ozols, R. F., *Cancer Res.*, 1985, 45, 2110-2115.) Ipomoeassins A-C and E (1-3 and 5) were moderately active, with IC$_{50}$ values ranging from 0.5 to 3.3 µM (Table 3). Interestingly ipomoeassin D (4), which differs from ipomoeassin C (3) only by an acetyl group, is almost two orders of magnitude more cytotoxic than 3, with an IC$_{50}$ value of 35 nM. The fully acetylated compounds 6 and 7 were significantly less active than the ipomoeassins, with IC$_{50}$ values of 15.8 and 19.1 µM. All this suggests that relatively minor structural variations may make significant differences to cytotoxicity and possibly other activities also. Compound also 14 exhibited potent cytotoxic activity with an IC$_{50}$ value of 0.036 µM, which was much more active than compound 1. Here we can see again that sometimes a slight modification of the structure will enhance the activity dramatically.

TABLE 3

Cytotoxicities of Compounds 1-7 and 14[a]

| compound | 1 | 2 | 3 | 4 | 5 | 6 | 7 | 14 |
|---|---|---|---|---|---|---|---|---|
| IC$_{50}$ (µM) | 0.5 | 0.4 | 2.9 | 0.035 | 3.3 | 15.8 | 19.1 | 0.036 |

[a]Concentration of each compound that inhibited 50% (IC$_{50}$) of the growth of the A2780 human ovarian cell line according to the procedure described.[12] Actinomycin D (IC$_{50}$ 0.8-2.4 nM) was the positive control.

A recent paper describes the X-ray crystal structure of tricolorin A, a compound isolated from *I. tricolor* (Rencurosi, A.; Mithchell, E. P.; Cioco, G.; Perez, S. W.; Pereda-Mitanda, R.; Imberty, A., *Angew. Chem., Int. Ed.*, 2004, 43, 5918-5922), and proposes that this structure supports the hypothesis that the cytotoxic activity of compounds of this class is due to their ability to form pores in cell membranes. Although this is certainly possible, this hypothesis by Rencurosi et al. does not fully explain why our inventive compounds that are closely similar to the tricolorin A compound show such different cytotoxicities; this Example 1 thus raises the possibility that other mechanisms of action are involved.

Experimental Procedures. Optical rotations were recorded on a Perkin-Elmer 241 polarimeter. IR and UV spectra were measured on MIDAC M-series FTIR and Shimadzu UV-1201 spectrophotometers, respectively. NMR spectra were obtained on a JEOL Eclipse 500 or a Unity 400 spectrometer in C$_6$D$_6$ or CDCl$_3$. Mass spectra were obtained on a JEOL JMS-HX-110 instrument, in the positive ion mode. The chemical shifts are given in δ (ppm), and coupling constants are reported in Hz. A Horizon™ Flash Chromatograph from BioTage Inc. was used for flash column chromatography. HPLC was performed on a Shimadzu LC-10AT instrument with a semi-preparative C18 or Phenyl Varian Dynamax column (5 µ, 250×10 mm) and a preparative C18 Varian Dynamax column (8 µ, 250×21.4 mm). Finnigan LTQ LC/MS'' with a C18 Hypersil column (5 µ, 100×2.1 mm) was used for crude sample analysis.

Cytotoxicity Bioassays. Cytotoxicity measurements were performed against the A2780 ovarian cancer cell line as previously described. The A2780 cell line is a drug-sensitive ovarian cancer cell line.

Plant Material. Leaves of *Ipomoea squamosa* Choisy (Convolvulaceae) were collected in Sipaliwini, Suriname in 1994, on the south side of Kuruni Island, on a riverbank east of the trail from camp to a canoe landing on the south branch of the Kuruni River around island, ca. 30 airline km east of its confluence on the Corantijn River at 180 m in elevation. Collection was made on 25 Nov. 1994, and the sample was designated Evans 2000. Voucher specimens have been deposited in the National Herbarium of Suriname and at the Missouri Botanical Garden. The plant material was extracted at Bedrijf Geneesmiddelen Voorziening Suriname with EtOAc to give extract E940631.

Isolation. The crude extract (10 g, IC$_{50}$: 8.0 µg/mL) of E940631 was separated using Biotage's Horizon high performance flash chromatograph over C18 using MeCN—H$_2$O (75:25, 420 mL) and then 100% MeOH (210 mL), furnishing thirty tubes (21 mL/tube). Based on Si-gel TLC (DCM: MeOH, 20:1), these thirty tubes were combined into five fractions (I-V), of which fraction III (800 mg) was found to be the most active (IC$_{50}$: 0.2 µg/mL). Five peaks were collected from fraction III using HPLC chromatography over C18 using 75% MeCN/H$_2$O, and ipomoeassin A (1, 60 mg, t$_R$ 26 min), ipomoeassin B (2, 6 mg, t$_R$ 16 min), and ipomoeassin E (5, 5 mg, t$_R$ 14 min) were isolated as pure components. Ipomoeassins C and D (collected from C18 HPLC eluting with 75% MeCN/H$_2$O, t$_R$ 10 and 23 min respectively) were further purified on normal-phase (DCM:MeOH, 20:1) TLC (3, 4 mg, Rf 0.3) and reverse-phase (MeCN:H$_2$O, 92:8) phenyl HPLC (4, 7 mg, t$_R$ 18 min). Further HPLC purification (C18, 75% MeCN/H$_2$O) of the fraction eluting just after compound 1 gave ipomoeassin F (14).

Ipomoeassin A (1): colorless oil; [α]$_D^{25}$ –36° (c 0.2, EtOH); IR (film) ν$_{max}$ 3414, 2928, 2858, 1721, 1636, 1450, 1380, 1250, 1152, 1134, 1071; UV (EtOH) λ$_{max}$ (log ε) 280 (3.90) nm; $^1$H NMR (500 MHz, C$_6$D$_6$) and $^{13}$C NMR (125

MHz, C$_6$D$_6$) data, see Tables 1 and 2 respectively; HRESIMS m/z 803.3854 (calcd for C$_{42}$H$_{59}$O$_{15}$, 803.3854).

Ipomoeassin B (2): colorless oil; [α]$_D^{25}$ –39° (c 0.3, EtOH); IR (film) ν$_{max}$ 3400, 2929, 2853, 1743, 1717, 1630, 1449, 1370, 1315, 1266, 1248, 1155, 1137, 1071; UV (EtOH) λ$_{max}$ (log ε) 280 (4.04) nm; $^1$H NMR (500 MHz, C$_6$D$_6$) and $^{13}$C NMR (125 MHz, C$_6$D$_6$) data, see Tables 1 and 2 respectively; HRESIMS m/z 761.3729 (calcd for C$_{40}$H$_{57}$O$_{14}$ 761.3748).

Ipomoeassin C (3): colorless oil; [α]$_D^{25}$ –290 (c 0.4, EtOH); IR (film) ν$_{max}$ 3400, 2930, 2855, 1721, 1637, 1450, 1380, 1249, 1154, 1074; UV (EtOH) λ$_{max}$ (log ε) 280 (3.80) nm; $^1$H NMR (500 MHz, C$_6$D$_6$) and $^{13}$C NMR (125 MHz, C$_6$D$_6$) data, see Tables 1 and 2 respectively; HRESIMS m/z 819.3806 (calcd for C$_{42}$H$_{59}$O$_{16}$ 819.3803).

Ipomoeassin D (4): colorless oil; [α]$_D^{25}$ –35° (c 0.2, EtOH); IR (film) ν$_{max}$ 3409, 2933, 2864, 1723, 1636, 1450, 1374, 1239, 1154, 1072; UV (EtOH) λ$_{max}$ (log ε) 280 (4.29) nm; $^1$H NMR (500 MHz, C$_6$D$_6$) and $^{13}$C NMR (125 MHz, C$_6$D$_6$) data, see Tables 1 and 2 respectively; HRESIMS m/z 861.3909 (calcd for C$_{44}$H$_{61}$O$_{17}$, 861.3909).

Ipomoeassin E (5): colorless oil; [α]$_D^{25}$ –24° (c 0.2, EtOH); IR (film) ν$_{max}$ 3400, 2930, 2855, 1721, 1637, 1449, 1370, 1308, 1249, 1154, 1071; UV (EtOH) λ$_{max}$ (log ε) 280 (4.06) nm; $^1$H NMR (500 MHz, C$_6$D$_6$) and $^{13}$C NMR (125 MHz, C$_6$D$_6$) data, see Tables 1 and 2 respectively; HRESIMS m/z 819.3784 (calcd for C$_{42}$H$_{59}$O$_{16}$ 819.3803).

Ipomoeasssin F (14): colorless oil; HR FABMS [M+1]$^+$ m/z 831.4211 (calcd for C$_{44}$H$_{63}$O$_{15}$ 831.4167), 28 amu more than ipomoeassin A (1). IR and UV spectra similar to those of compound 1.

Preparation of derivatives 6 and 7: Ipomoeassins A-E (1-5, 1 mg each) were independently acetylated with Ac$_2$O-pyridine (1:1). Compounds 1 and 2 yielded 6, while ipomoeassins C-E (3-5) gave 7. Derivatives 6 (1.0 and 1.1 mg from 1 and 2 respectively, t$_R$ 17 min) and 7 (1.1, 1.0 and 1.1 mg from 3, 4 and 5 respectively t$_R$ 19 min) were purified by C18 HPLC [Varian Dynamax column (8μ, 250×21.4 mm), 2 mL/min, 85% MeOH/H$_2$O]. In each case the identities of the acetylated products were confirmed by comparison of $^1$H NMR data, optical rotations, MS and HPLC retention times.

3',2"-O-Diacetyl ipomoeassin A (6): colorless oil; [α]$_D^{25}$ –26° (c 0.1, EtOH); $^1$H NMR (500 MHz, C$_6$D$_6$): δ$_H$ 7.78 (1H, d, J=16.1 Hz, H-CA-3), 6.88-7.02 [6H, mm H-TA-3,CA-5(×2),6(×2),7], 6.36 (1H, d, J=16.1 Hz, H-CA-2), 5.71 (1H, t, J=9.7 Hz, H-3" or 4"), 5.63 (1H, t, J=9.7 Hz, H-4" or 3"), 5.45 (1H, dd, J=9.7, 8.0 Hz, H-2"), 5.31 (1H, d, J=3.5 Hz, H-4'), 5.15 (1H, dd, J=10.2, 3.5 Hz, H-3'), 4.96 (1H, d, J=8.0 Hz, H-1"), 4.53 (1H, dd, J=12.6, 3.0 Hz, H-6"), 4.30 (1H, d, J=7.6 Hz, H-1'), 4.12 (1H, dd, J=10.2, 7.6 Hz, H-2'), 4.02 (1H, dd, J=12.6, 2.3 Hz, H-6"), 3.59 (1H, m, H-11), 3.15 (1H, br d, J=9.7 Hz, H-5"), 3.07 (1H, br q, J=6.5 Hz, H-5'), 2.70 & 2.21 (2H, m, H$_2$-3), 2.70 & 2.52 (2H, m, H$_2$-2), 2.09 (1H, m, H-5), 2.03 (3H, s, Ac), 1.91 (3H, s, Ac), 1.74 (3H, br s, H$_3$-TA-5), 1.71 (3H, s, Ac), 1.30-1.80 (15H, m, H-5 & H$_2$-6,7,8,9,10,12, 13), 1.21 (3H, dd, J=7.1, 1.2 Hz, H$_3$-TA-4), 0.96 (3H, d, J=6.5 Hz, H$_3$-6"), 0.87 (3H, t, J=7.1 Hz, H$_3$-14); HRESIMS m/z 887.4108 (calcd for C$_{46}$H$_{63}$O$_{17}$ 887.4065).

5,3',2"-O-Triacetyl ipomoeassin C (7): colorless oil; [α]$_D^{25}$ –30° (c 0.1, EtOH);

$^1$H NMR (500 MHz, C$_6$D$_6$): δ$_H$ 7.77 (1H, d, J=16.1 Hz, H-CA-3), 6.88-7.02 [6H, m, H-TA-3,CA-5(×2),6(×2),7], 6.35 (1H, d, J=16.1 Hz, H-CA-2), 5.66 (1H, t, J=9.7 Hz, H-3" or 4|), 5.61 (1H, t, J=9.7 Hz, H-4" or 3"), 5.35 (1H, dd, J=9.7, 8.0 Hz, H-2"), 5.28 (1H, dd, J=3.7, 1.4 Hz, H-4'), 5.15 (1H, dd, J=9.5, 4.4 Hz, H-5), 5.10 (1H, dd, J=10.1, 3.4 Hz, H-3'), 4.94 (1H, d, J=8.0 Hz, H-1"), 4.49 (1H, dd, J=12.4, 3.0 Hz, H-6"), 4.22 (1H, d, J=7.8 Hz, H-1'), 4.07 (1H, dd, J=10.1, 8.0 Hz, H-2'), 4.02 (1H, dd, J=12.4, 1.8 Hz, H-6"), 3.59 (1H, m, H-11), 3.16 (1H, br d, J=9.7 Hz, H-5"), 3.02 (1H, br q, J=6.5 Hz, H-5'), 2.92 & 2.50 (2H, m, H$_2$-3), 2.63 & 2.58 (2H, m, H$_2$-2), 2.09 (1H, m, H-5), 2.01 (3H, s, Ac), 1.89 (3H, s, Ac), 1.88 (3H, s, Ac), 1.72 (3H, br s, H$_3$-TA-5), 1.70 (3H, s, Ac), 1.30-1.80 (14H, m, H$_2$-6,7,8,9,10,12,13), 1.23 (3H, dd, J=7.1, 1.2 Hz, H$_3$-TA-4), 0.95 (3H, d, J=6.4 Hz, H$_3$-6"), 0.88 (3H, t, J=7.1 Hz, H$_3$-14); HRESIMS m/z 945.4141 (calcd for C$_{48}$H$_{65}$O$_{19}$ 945.4120).

Hydrolysis of 1: Approximately 40 mg of 1 was dissolved in 4 mL of freshly distilled THF and 6 mL of 1.0 M NaOH. The solution was refluxed for 3 h. The reaction was cooled to room temperature and acidified to pH 4 with 2.0 N HCl. This solution was extracted three times with 10 mL aliquots of ether. The ether extracts were combined and evaporated to dryness. A GC/CI-MS analysis identified two acids, cinnamic acid and 2-methyl but-2-enoic acid. To verify the identities, standard samples of the two acids were purchased and treated as above.

The aqueous-THF layer from the initial base hydrolysis was evaporated to dryness and dissolved in 4 mL of fresh THF containing 4 mL of 2.0 N HCl. The sample was refluxed for 4 h. The reaction was cooled to room temperature and extracted three times with 10 mL aliquots of ether. 11-Hydroxy-4-oxo-tetradecanoic acid (8, 5 mg) was deduced to be the major component in the ether extract on the basis of a main peak on C18 HPLC (MeOH:H$_2$O, 70:30; t$_R$: 17 min) and its HRES-IMS (m/z 259.1907, calcd for C$_{14}$H$_{27}$O$_4$, 259.1909). 11-Hydroxy-4-oxo-tetradecanoic acid (8, 4.0 mg) was reacted with excess diazomethane to furnish 11-hydroxy-4-oxo-tetradecanoic acid methyl ester (9, 4 mg).

Sugar analysis of 1: The aqueous layer was neutralized with 1 M NaOH and extracted with n-BuOH (3×4 mL). The n-BuOH extract was evaporated to afford about 10 mg of a mixture of monosaccharides, which was subjected to TLC [CHCl$_3$-MeOH—H$_2$O (6:4:1): R$_f$; 0.4 (D-glucose); 0.6 (D-fucose)] and HPLC [Varian Dynamax NH$_2$, 5μ, 250×10 mm, 2 mL/min; 70% MeCN/H$_2$O; Light Scattering Detector (Dedex 75, Sedere); D-glucose: 1 mg, t$_R$=19 min; D-fucose: 1 mg, t$_R$=14.6 min] analysis. The absolute configurations of the sugars were determined by their rotations. Glucose had [α]$_D^{19}$ +114° (c 0.1, H$_2$O) and fucose had [α]$_D^{19}$ +116° (c 0.09, H$_2$O). An aliquot of the hydrolysis mixture was derived with Sigma Sil-A for 35 min at 70° C. GC-MS analysis [Varian GC column, VF-5MS; 30 m×0.32 mm (i.d.); film thickness, 0.25 mm; 80° C. to 280° C. at 80° C./min; injection temperature, 200° C.] allowed the identification of the following TMS-sugars by coelution with authentic samples: penta-TMS-glucose, t$_R$=16.3 min; tetra-TMS-fucose, t$_R$=13.2 min.

11-Hydroxy-4-oxo-tetradecanoic acid (8): colorless oil; [α]$_D^{25}$ –25° (c 0.1, EtOH); $^1$H NMR (500 MHz, CDCl$_3$): δ$_H$ 3.60 (1H, m, H-11), 2.73 (2H, m, H-3), 2.64 (2H, m, H-2), 2.45 (2H, t, J=7.3 Hz, H-5), 1.60 (2H, m, H-6), 1.30-1.48 (12H, m, H$_2$-7-H$_2$-10, H$_2$-12 and H$_2$-13), 0.93 (3H, t, J=7.0 Hz, H-14); $^{13}$C NMR (125 MHz, CDCl$_3$): δ$_C$ 209.5 (C-4), 175.8 (C-1), 71.7 (C-11), 42.6 (C-5), 39.6 (C-12), 37.3 (C-10), 37.0 (C-2), 29.7 (C-8), 29.3 (C-7), 29.0 (C-3), 25.3 (C-9), 23.6 (C-6), 18.8 (C-13), 14.1 (C-14); HRESIMS m/z 259.1907 (calcd for C$_{14}$H$_{27}$O$_4$, 259.1909).

11-Hydroxy-4-oxo-tetradecanoic acid methyl ester (9): colorless oil; [α]$_D$$^{25}$ −4° (c 0.1, EtOH); $^1$H NMR (500 MHz, CDCl$_3$): δ$_H$ 3.67 (3H, s, OMe), 3.59 (1H, m, H-11), 2.71 (2H, t, J=6.3 Hz, H-3), 2.59 (2H, t, J=6.3 Hz, H-2), 2.45 (2H, t, J=7.3 Hz, H-5), 1.59 (2H, m, H-6), 1.30-1.48 (12H, m, H$_2$-7-H$_2$-10, H$_2$-12 and H$_2$-13), 0.92 (3H, t, J=7.2 Hz, H-14); $^{13}$C NMR (125 MHz, CDCl$_3$): δ$_C$ 209.2 (C-4), 173.3 (C-1), 71.7 (C-11), 51.7 (OMe), 42.7 (C-5), 39.5 (C-12), 37.5 (C-10), 36.8 (C-2), 29.4 (C-8), 29.0 (C-7), 27.6 (C-3), 25.4 (C-9), 23.5 (C-6), 18.7 (C-13), 13.9 (C-14); HRESIMS m/z 273.2066 (calcd for C$_{15}$H$_{29}$O$_4$, 273.2066).

Mosher esters 10 and 11: To a solution of (R)-MPA (6.0 mg) and DMAP (5.0 mg) in CH$_2$Cl$_2$ (0.5 mL) was added 11-hydroxy-4-oxo-tetradecanoic acid methyl ester (9, 1 mg) in CH$_2$Cl$_2$ (0.5 mL), followed by EDCI (5.0 mg) and the resulting solution was stirred for 12 h. EtOAc was then added to quench the reaction and the solution concentrated. The resulting residue was purified on C18 HPLC, eluting with MeOH/H$_2$O, 85:15 to give 10 (1.5 mg, 97%, t$_R$ 12 min). Treatment of 9 with (S)-MPA by the same procedure as described above, and eluting with MeOH/H$_2$O, 80:20, yielded 11 (1.2 mg, 78%, t$_R$ 17 min).

11-(R-MPA)-4-oxo-tetradecanoic acid methyl ester (10): colorless oil; [α]$_D$$^{25}$ −13° (c 0.1, EtOH); $^1$H NMR (500 MHz, CDCl$_3$): δ$_H$ 7.44 (2H, m), 7.35 (3H, m), 4.90 (1H, m, H-11), 4.73 (1H, s), 3.67 (3H, s, 1-OMe), 3.42 (3H, s, OMe), 2.72 (2H, t, J=6.4 Hz, H-3), 2.59 (2H, t, J=6.4 Hz, H-2), 2.43 (2H, t, J=7.3 Hz, H-5), 1.49 (2H, m, H$_2$-10), 1.38 (2H, m, H$_2$-12), 1.15-1.30 (6H, m, H$_2$-6-H$_2$-8), 1.23 (2H, m, H$_2$-9), 0.98 (2H, m, H$_2$-13), 0.71 (3H, t, J=7.4 Hz, H$_3$-14); HRESIMS m/z 421.2574 (calcd for C$_{24}$H$_{37}$O$_6$ 421.2590).

11-(S-MPA)-4-oxo-tetradecanoic acid methyl ester (11): colorless oil; [α]$_D$$^{25}$ −2° (c 0.1, EtOH); $^1$H NMR (500 MHz, CDCl$_3$): δ$_H$ 7.44 (2H, m), 7.35 (3H, m), 4.91 (1H, m, H-11), 4.72 (1H, s), 3.67 (3H, s, 1-OMe), 3.41 (3H, s, OMe), 2.71 (2H, t, J=6.4 Hz, H-3), 2.59 (2H, t, J=6.4 Hz, H-2), 2.38 (2H, t, J=7.3 Hz, H-5), 1.46 (2H, m, H$_2$-12), 1.37 (2H, m, H$_2$-10), 1.27 (2H, m, H$_2$-13), 1.00-1.10 & 1.00-1.10 (6H, m, H$_2$-6-H$_2$-8), 0.91 (2H, m, H$_2$-9), 0.88 (3H, t, J=7.4 Hz, H$_3$-14); HRESIMS m/z 421.2607 (calcd for C$_{24}$H$_{37}$O$_6$ 421.2590).

Mosher esters 12 and 13: To a solution of (R)-MPA (6.0 mg) and DMAP (5.0 mg) in CH$_2$Cl$_2$ (0.5 mL) was added 3 (1 mg) in CH$_2$Cl$_2$ (0.5 mL), followed by EDCI (5.0 mg) and the resulting solution was stirred for 12 h. EtOAc was then added to quench the reaction and the solution concentrated. The resulting residue was purified on C18 HPLC, eluting with MeCN/H$_2$O, 85:15, to give 12 (1.3 mg, 95%, t$_R$ 17 min). Treatment of 3 with (S)-MPA by the same procedure described above yielded 13 (1 mg, 75%, t$_R$ 18.5 min).

5-(R-MPA)-ipomoeassin C (12): colorless oil; [α]$_D$$^{25}$ −8° (c 0.1, EtOH); $^1$H NMR (500 MHz, CDCl$_3$): δ$_H$ 7.64 (1H, d, J=16.0 Hz, H-CA-3), 7.30-7.55 (15H, m), 6.86 (1H, m, H-TA-3), 6.36 (1H, d, J=16.0 Hz, H-CA-2), 5.25 (3H, m, H-3",4α,4'), 5.06 (1H, dd, J=6.2, 4.2 Hz, H-5), 4.78 (1H, dd, J=10.3, 3.4 Hz, H-3'), 4.90 (1H, s), 4.78 (1H, s), 4.61 (1H, d, J=7.8 Hz, H-1"), 4.42 (1H, d, J=7.8 Hz, H-1'), 4.37 (1H, dd, J=12.2, 3.2 Hz, H-6"), 4.15 (1H, dd, J=12.2, 3.0 Hz, H-6"), 3.99 (1H, dd, J=10.3, 7.8 Hz, H-2'), 3.72 (2H, m, H-5',5"), 3.65 (1H, m, H-11), 3.50 (1H, m, H-2"), 3.44 (3H, s, OMe), 3.31 (3H, s, OMe), 2.82 & 2.69 (2H, m, H$_2$-3), 2.69 & 2.53 (2H, m, H$_2$-2), 1.97 (3H, s, Ac), 1.77 (3H, br s, H$_3$-TA-5), 1.75 (1H, m, H$_2$-7), 1.71 (3H, dd, J=7.2, 1.2 Hz, H$_3$-TA-4), 1.69 (1H, m, H$_2$-6), 1.20-1.90 (10H, m, H$_2$-8,9,10,12,13), 1.13 (3H, d, J=6.5 Hz, H$_3$-6"), 0.90 (3H, t, J=7.1 Hz, H$_3$-14); HRESIMS m/z 1115.4899 (calcd for C$_{60}$H$_{75}$O$_{20}$ 1115.4852).

5-(S-MPA)-ipomoeassin C (13): colorless oil; [α]$_D$$^{25}$ −4° (c 0.1, EtOH); $^1$H NMR (500 MHz, CDCl$_3$): δ$_H$ 7.61 (1H, d, J=16.0 Hz, H-CA-3), 7.30-7.55 (15H, m), 6.87 (1H, m, H-TA-3), 6.34 (1H, d, J=16.0 Hz, H-CA-2), 5.25 (1H, t, J=9.9 Hz, H-3"), 5.21 (1H, d, J=5.0 Hz, H-4'), 5.16 (1H, t, J=9.9 Hz, H-4"), 5.09 (1H, dd, J=6.6, 3.4 Hz, H-5), 5.00 (1H, dd, J=11.5, 5.0 Hz, H-3'), 4.89 (1H, s), 4.76 (1H, s), 4.59 (1H, d, J=7.8 Hz, H-1"), 4.44 (2H, m, H-1',6"), 4.00 (2H, m, H-2',6"), 3.71 (2H, m, H-5',5"), 3.62 (1H, dd, J=12.2, 3.0 Hz, H-5"), 3.48 (3H, s, OMe), 3.37 (1H, m, H-2"), 3.34 (3H, s, OMe), 2.56 & 2.43 (2H, m, H$_2$-3), 2.43 & 2.13 (2H, m, H$_2$-2), 1.93 (3H, s, Ac), 1.81 (3H, br s, H$_3$-TA-5), 1.79 (1H, m, H$_2$-7), 1.73 (3H, d, J=7.2 Hz, H$_3$-TA-4), 1.72 (1H, m, H$_2$-6), 1.20-1.90 (10H, m, H$_2$-8,9,10,12,13), 1.10 (3H, d, J=6.5 Hz, H$_3$-6'), 0.90 (3H, t, J=7.4 Hz, H$_3$-14); HRESIMS m/z 1115.4852 (calcd for C$_{60}$H$_{75}$O$_{20}$ 1115.4852).

Thus, in this Example 1, glycoresins, ipomoeassins A-F (1-5, 14), have been isolated from the leaves of *Ipomoea squamosa*. The structures were elucidated by spectroscopic analyses and chemical transformations. The absolute configurations of C-5 (ipomoeassins 3-5) and C-11 (ipomoeassins 1 and 2) were determined by their derivatives with (R)- and (S)-MPA. All the isolates were active in the A2780 human ovarian cancer cell line assay, and 4 showed the highest activity with an IC$_{50}$ value of 35 nM. Novel compounds according to the following formula are therefore useful as anti-cancer agents:

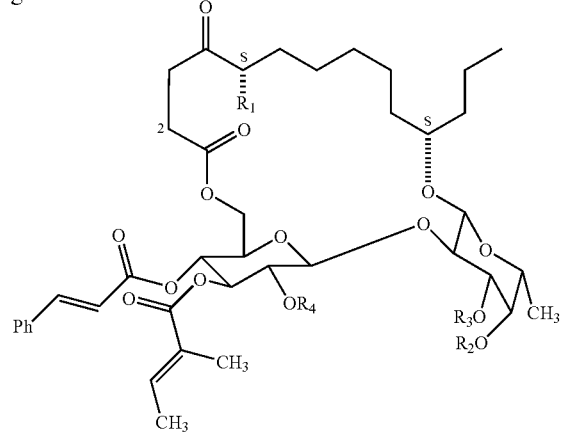

R$_1$=H, OH, or OAc; R$_2$, R$_3$, R$_4$,=H or Ac

Example 2

*Ipomoea squamosa* (Convolvulaceae) E940631, A2780

Inventive compounds 1-7 and 14 were studied.

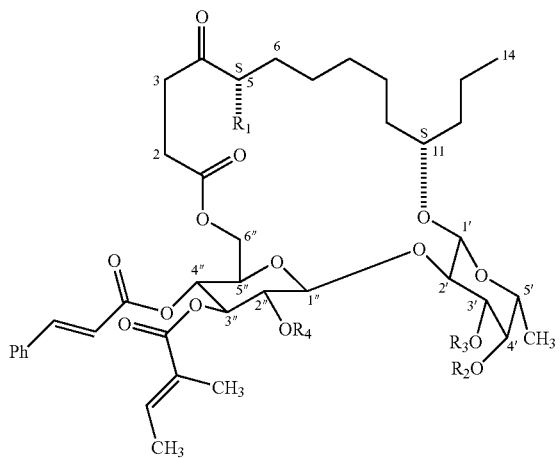

1  $R_1 = R_3 = R_4 = H$; $R_2 = Ac$;
2  $R_1 = R_2 = R_3 = R_4 = H$
3  $R_1 = OH$; $R_2 = Ac$; $R_3 = R_4 = H$
4  $R_1 = OAc$; $R_2 = Ac$; $R_3 = R_4 = H$
5  $R_1 = OAc$; $R_2 = R_3 = R_4 = H$
6  $R_1 = H$; $R_2 = R_3 = R_4 = Ac$
7  $R_1 = OAc$; $R_2 = R_3 = R_4 = Ac$

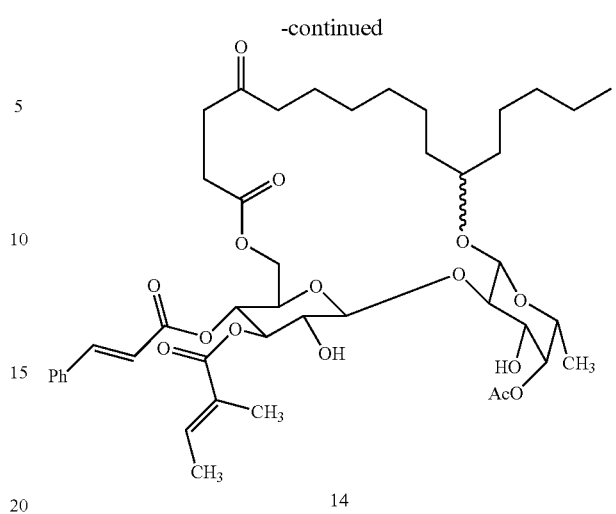

Chemical names and formulae of the inventive compounds mentioned above are summarized as follows in Table 4.

TABLE 4

Compound Names and Formulae

| Cpd No | Short Name | Chemical Abstracts name | Composition |
|---|---|---|---|
| 1 | ipomoeassin A | Tetradecanoic acid, 11-[[4-O-acetyl-6-deoxy-2-O-[3-O-[(2E)-2-methyl-1-oxo-2-butenyl]-4-O-[(2E)-1-oxo-3-phenyl-2-propenyl]-β-D-glucopyranosyl]-β-D-galactopyranosyl]oxy]-4-oxo-, intramol. 1,6″-ester, (11S)- | $C_{42}H_{58}O_{15}$ |
| 2 | ipomoeassin B | Tetradecanoic acid, 11-[[6-deoxy-2-O-[3-O-[(2E)-2-methyl-1-oxo-2-butenyl]-4-O-[(2E)-1-oxo-3-phenyl-2-propenyl]-β-D-glucopyranosyl]-β-D-galactopyranosyl]oxy]-4-oxo-, intramol. 1,6″-ester, (11S)- | $C_{40}H_{56}O_{14}$ |
| 3 | ipomoeassin C | Tetradecanoic acid, 11-[[4-O-acetyl-6-deoxy-2-O-[3-O-[(2E)-2-methyl-1-oxo-2-butenyl]-4-O-[(2E)-1-oxo-3-phenyl-2-propenyl]-β-D-glucopyranosyl]-β-D-galactopyranosyl]oxy]-5-hydroxy-4-oxo-, intramol. 1,6″-ester, (5S,11S)- | $C_{42}H_{58}O_{16}$ |
| 4 | ipomoeassin D | Tetradecanoic acid, 11-[[4-O-acetyl-6-deoxy-2-O-[3-O-[(2E)-2-methyl-1-oxo-2-butenyl]-4-O-[(2E)-1-oxo-3-phenyl-2-propenyl]-β-D-glucopyranosyl]-β-D-galactopyranosyl]oxy]-5-(acetyloxy)-4-oxo-, intramol. 1,6″-ester, (5S,11S)- | $C_{44}H_{60}O_{17}$ |
| 5 | ipomoeassin E | Tetradecanoic acid, 5-(acetyloxy)-11-[[6-deoxy-2-O-[3-O-[(2E)-2-methyl-1-oxo-2-butenyl]-4-O-[(2E)-1-oxo-3-phenyl-2-propenyl]-β-D-glucopyranosyl]-β-D-galactopyranosyl]oxy]-4-oxo-, intramol. 1,6″-ester, (5S,11S)- | $C_{42}H_{58}O_{16}$ |
| 6 | 3′,2″-O-Diacetyl ipomoeassin A | | |
| 7 | 5,3′,2″-O-Triacetyl ipomoeassin C | | |
| 8 | 11-hydroxy-4-oxo-tetradecanoic acid | | |
| 9 | 11-hydroxy-4-oxo-tetradecanoic acid methyl ester | | |
| 10 | 11-(R-MPA)-4-oxo-tetradecanoic acid methyl ester | | |
| 11 | 11-(S-MPA)-4-oxo-tetradecanoic acid methyl ester | | |

TABLE 4-continued

Compound Names and Formulae

| Cpd No | Short Name | Chemical Abstracts name | Composition |
|---|---|---|---|
| 12 | 5-(R-MPA)-ipomoeassin C | | |
| 13 | 5-(S-MPA)-ipomoeassin C | | |
| 14 | Ipomoeassin F | Hexadecanoic acid, 11-[[4-O-acetyl-6-deoxy-2-O-[3-O-[(2E)-2-methyl-1-oxo-2-butenyl]-4-O-[(2E)-1-oxo-3-phenyl-2-propenyl]-β-D-glucopyranosyl]-β-D-galactopyranosyl]oxy]-4-oxo-, intramol. 1,6''-ester, (11S)- | $C_{44}H_{62}O_{15}$ |

While the invention has been described in terms of its preferred embodiments, those skilled in the art will recognize that the invention can be practiced with modification within the spirit and scope of the appended claims.

What we claim as our invention is:

1. An isolated compound selected from the group consisting of:

(1) a compound of structure 1:

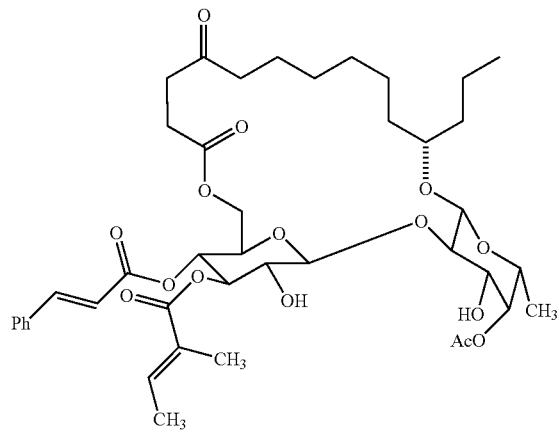

(2) a compound of structure 2:

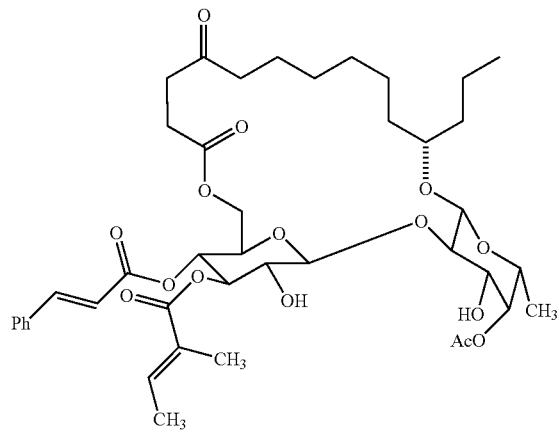

(3) a compound of structure 3:

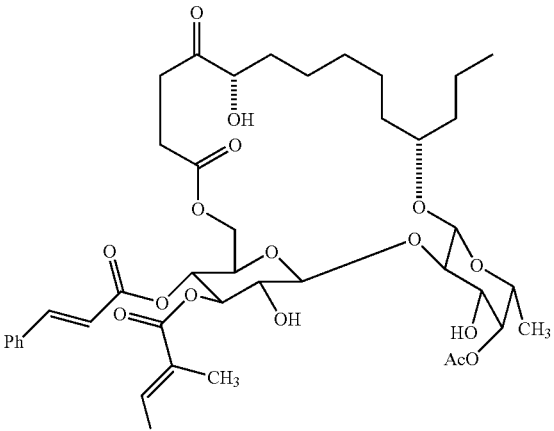

(4) a compound of structure 4:

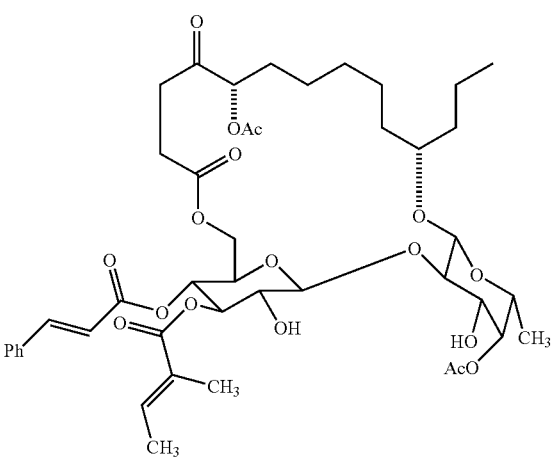

(5) a compound of structure 5:

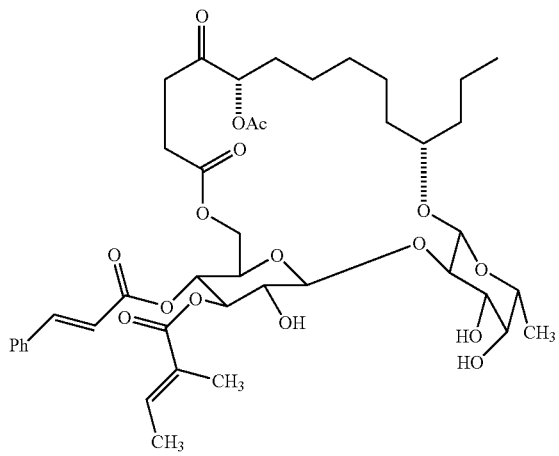

(6) a compound of structure 6:

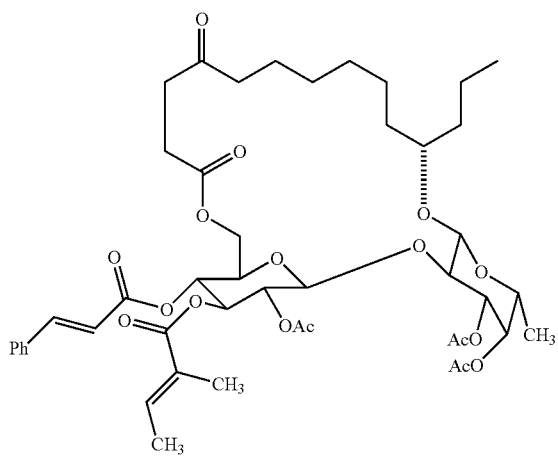

(7) a compound of structure 7:

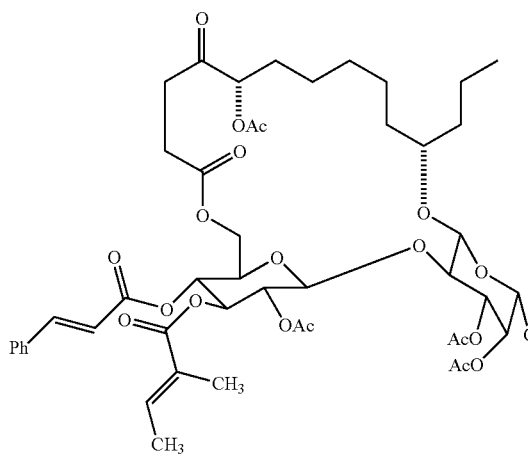

(8) a compound of structure 14:

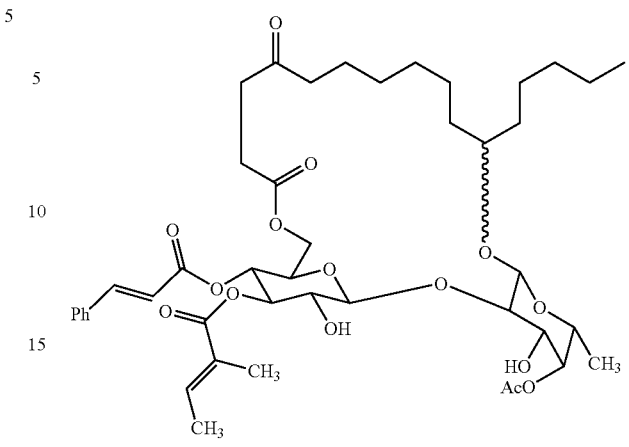

(9) a compound of structure 15:

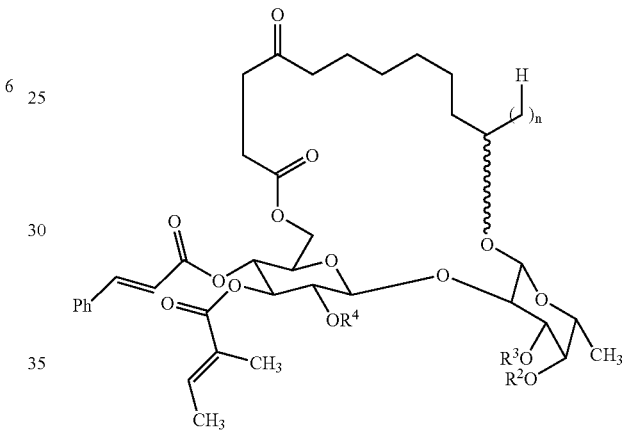

wherein $R^2$, $R^3$, and $R^4$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups, $R^2$, $R^3$, and $R^4$ can be the same or different groups, and n can be any integer from 0 to 10;

(10) a compound of structure 16:

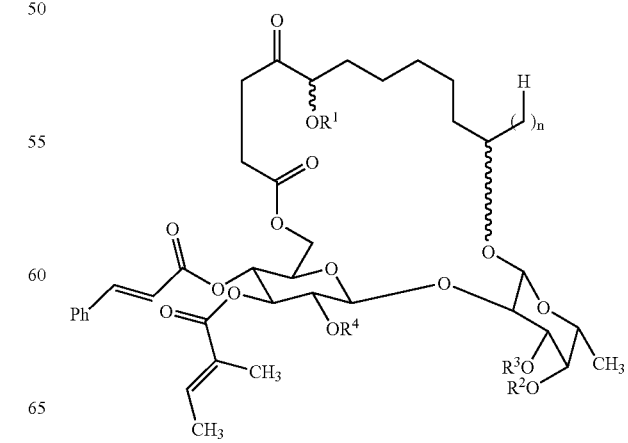

wherein $R^1$, $R^2$, $R^3$, and $R^4$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups, $R^1$, $R^2$, $R^3$, and $R^4$ can be the same or different groups, and n can be any integer from 0 to 10;

(11) a compound of structure 17:

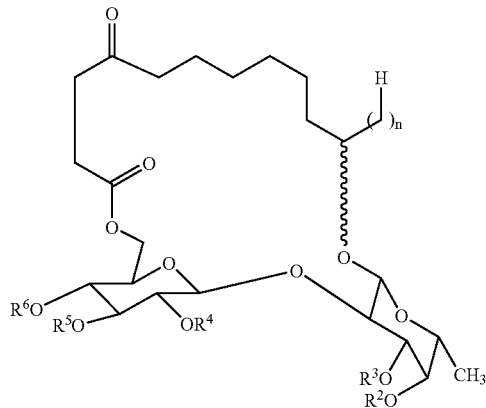

17 wherein $R^2$, $R^3$, $R^4$, $R^5$, and $R^6$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups, $R^2$, $R^3$, $R^4$, $R^5$, and $R^6$ can be the same or different groups, and n can be any integer from 0 to 10; and

(12) a compound of structure 18:

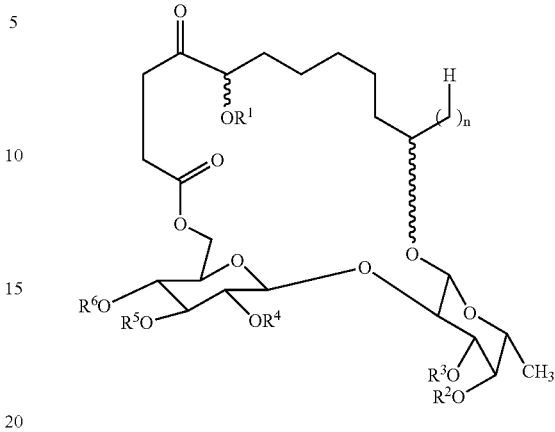

18 wherein $R^1$, $R^2$, $R^3$, $R^4$, $R^5$, and $R^6$ can variously be hydrogen or can be drawn from the groups WCO, where W can be hydrogen, any $C_1$ to $C_{12}$ straight chain or branched alkyl group, any aryl group, or any alkenyl group in which the double bond can be variously substituted with $C_1$ to $C_6$ alkyl groups, aryl groups, or a combination of alkyl and aryl groups, $R^1$, $R^2$, $R^3$, $R^4$, $R^5$, and $R^6$ can be the same or different groups, and n can be any integer from 0 to 10.

2. A pharmaceutical composition comprising: at least one compound selected from the group consisting of structures (1), (2), (3), (4), (5), (6), (7), (14), (15), (16), (17), and (18), together with an emulsifying agent, wherein the pharmaceutical composition is suitable for human drug use.

3. The pharmaceutical composition of claim 2 further comprising an alcohol.

* * * * *